US011225682B2

(12) United States Patent
Reichert et al.

(10) Patent No.: US 11,225,682 B2
(45) Date of Patent: Jan. 18, 2022

(54) AUTOMATED METHOD FOR ISOLATION, SELECTION AND/OR DETECTION OF MICROORGANISMS OR CELLS COMPRISED IN A SOLUTION

(71) Applicant: CureVac AG, Tübingen (DE)

(72) Inventors: Isabel Reichert, Nürtingen-Oberensingen (DE); Fabian Johannes Eber, Tübingen (DE); Christian Mayer, Pfullingen (DE); Aniela Wochner, Tübingen (DE)

(73) Assignee: CureVac AG, Tübingen (DE)

( * ) Notice: Subject to any disclaimer, the term of this patent is extended or adjusted under 35 U.S.C. 154(b) by 314 days.

(21) Appl. No.: 15/767,481

(22) PCT Filed: Oct. 12, 2016

(86) PCT No.: PCT/EP2016/074515
§ 371 (c)(1),
(2) Date: Apr. 11, 2018

(87) PCT Pub. No.: WO2017/064146
PCT Pub. Date: Apr. 20, 2017

(65) Prior Publication Data
US 2019/0249219 A1 Aug. 15, 2019

(30) Foreign Application Priority Data
Oct. 12, 2015 (WO) .................. PCT/EP2015/073559

(51) Int. Cl.
*C12Q 1/20* (2006.01)
*C12Q 1/24* (2006.01)
*C12N 1/20* (2006.01)
(52) U.S. Cl.
CPC .................. *C12Q 1/24* (2013.01); *C12N 1/20* (2013.01); *C12Q 1/20* (2013.01)

(58) Field of Classification Search
None
See application file for complete search history.

(56) References Cited

U.S. PATENT DOCUMENTS

2002/0090720 A1* 7/2002 Mutz .................. G01N 35/1074
435/325
2003/0052943 A1* 3/2003 Ellson .................. B01J 19/0046
347/46

(Continued)

FOREIGN PATENT DOCUMENTS

WO WO 2017/021546 2/2017
WO WO 2017/025447 2/2017

(Continued)

OTHER PUBLICATIONS

Demirci et al. "Single cell epitaxy by acoustic picolitre droplets" Lab Chip, 2007, 7, 1139-1145. (Year: 2007).*

(Continued)

*Primary Examiner* — Marcia S Noble
*Assistant Examiner* — Lauren K Van Buren
(74) *Attorney, Agent, or Firm* — Parker Highlander PLLC

(57) ABSTRACT

The present invention is concerned with an automated method for obtaining at least one discrete colony from microorganisms or cells comprised in a solution. This method includes a step where acoustic liquid transfer is employed. The present invention further relates to the use of an acoustic liquid transfer device for obtaining at least one discrete colony from micro organisms or cells comprised in a solution. The present invention also relates to an automated method for determining the presence and/or quantity of microorganisms or cells potentially comprised in a solution and to the use of an acoustic liquid transfer device for determining the presence and/or quantity of microorganisms or cells potentially comprised in a solution.

11 Claims, 6 Drawing Sheets

A)

B)

(56) References Cited

U.S. PATENT DOCUMENTS

| | | |
|---|---|---|
| 2005/0032730 A1 | 2/2005 | von der Mülbe et al. |
| 2005/0059624 A1 | 3/2005 | Hoerr et al. |
| 2005/0250723 A1 | 11/2005 | Hoerr et al. |
| 2006/0188490 A1 | 8/2006 | Hoerr et al. |
| 2008/0025944 A1 | 1/2008 | Hoerr et al. |
| 2008/0267873 A1 | 10/2008 | Hoerr et al. |
| 2009/0324584 A1 | 12/2009 | Hoerr et al. |
| 2010/0048883 A1 | 2/2010 | Ketterer et al. |
| 2010/0189729 A1 | 7/2010 | Hoerr et al. |
| 2010/0203076 A1 | 8/2010 | Fotin-Mleczek et al. |
| 2010/0291156 A1 | 11/2010 | Barner et al. |
| 2010/0305196 A1 | 12/2010 | Probst et al. |
| 2011/0053829 A1 | 3/2011 | Baumhof et al. |
| 2011/0250225 A1 | 10/2011 | Fotin-Mleczek et al. |
| 2012/0021043 A1 | 1/2012 | Kramps et al. |
| 2012/0258046 A1 | 10/2012 | Mutzke |
| 2013/0129754 A1 | 5/2013 | Thess et al. |
| 2013/0142818 A1 | 6/2013 | Baumhof et al. |
| 2013/0236901 A1* | 9/2013 | Potier .............. C12Q 1/6806 435/6.12 |
| 2013/0259879 A1 | 10/2013 | Baumhof et al. |
| 2013/0280283 A1 | 10/2013 | Lorenz et al. |
| 2013/0295043 A1 | 11/2013 | Kallen et al. |
| 2013/0336998 A1 | 12/2013 | Kallen et al. |
| 2015/0037326 A1 | 2/2015 | Butler-Ransohoff et al. |
| 2015/0050302 A1 | 2/2015 | Thess |
| 2015/0057340 A1 | 2/2015 | Thess et al. |
| 2015/0093413 A1 | 4/2015 | Thess et al. |
| 2015/0118183 A1 | 4/2015 | Baumhof |
| 2015/0118264 A1 | 4/2015 | Baumhof et al. |
| 2015/0165006 A1 | 6/2015 | Thess et al. |
| 2015/0184195 A1 | 7/2015 | Thess |
| 2015/0218554 A1 | 8/2015 | Thess |
| 2015/0306249 A1 | 10/2015 | Baumhof et al. |
| 2015/0320847 A1 | 11/2015 | Thess et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake |
| 2016/0304883 A1 | 10/2016 | Grund |
| 2016/0304938 A1 | 10/2016 | Wochner |
| 2016/0326575 A1 | 11/2016 | von der Mülbe |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |
| 2017/0252430 A1 | 9/2017 | Fotin-Mleczek |
| 2017/0326225 A1 | 11/2017 | Rauch |
| 2018/0044687 A1 | 2/2018 | Thess et al. |
| 2018/0125952 A1 | 5/2018 | Fotin-Mleczek |
| 2018/0126003 A1 | 5/2018 | Hoerr |
| 2018/0142275 A1 | 5/2018 | Roos et al. |
| 2018/0147146 A1 | 5/2018 | Eber et al. |
| 2018/0148727 A1 | 5/2018 | Grund |
| 2018/0201967 A1 | 7/2018 | Eber et al. |
| 2018/0208957 A1 | 7/2018 | Roos et al. |
| 2018/0214537 A1 | 8/2018 | Mutzke et al. |
| 2018/0237786 A1 | 8/2018 | Schlake |
| 2018/0237817 A1 | 8/2018 | Roos et al. |
| 2018/0243219 A1 | 8/2018 | Ketterer et al. |
| 2018/0296663 A1 | 10/2018 | Hipp et al. |
| 2018/0298372 A1 | 10/2018 | Funkner et al. |
| 2018/0312545 A1 | 11/2018 | Baumhof et al. |
| 2018/0371392 A1 | 12/2018 | Mayer |
| 2019/0010485 A1 | 1/2019 | Yazdan Panah et al. |
| 2019/0017100 A1 | 1/2019 | Wochner |
| 2019/0024096 A1 | 1/2019 | Schmid et al. |
| 2019/0040378 A1 | 2/2019 | Fotin-Mleczek et al. |
| 2019/0049414 A1 | 2/2019 | Wochner et al. |
| 2019/0083602 A1 | 3/2019 | Roos et al. |
| 2019/0100784 A1 | 4/2019 | Eber et al. |
| 2019/0125857 A1 | 5/2019 | Rauch et al. |
| 2019/0133950 A1 | 5/2019 | Eber et al. |

FOREIGN PATENT DOCUMENTS

| | | |
|---|---|---|
| WO | WO 2017/081110 | 5/2017 |
| WO | WO 2017/137095 | 8/2017 |
| WO | WO 2017/140905 | 8/2017 |
| WO | WO 2017/162297 | 9/2017 |
| WO | WO 2017/182634 | 10/2017 |
| WO | WO 2017/186928 | 11/2017 |
| WO | WO 2017/191258 | 11/2017 |
| WO | WO 2017/191274 | 11/2017 |
| WO | WO 2017/203008 | 11/2017 |
| WO | WO 2017/212006 | 12/2017 |
| WO | WO 2017/212007 | 12/2017 |
| WO | WO 2017/212008 | 12/2017 |
| WO | WO 2017/212009 | 12/2017 |
| WO | WO 2018/033254 | 2/2018 |
| WO | WO 2018/078053 | 5/2018 |

OTHER PUBLICATIONS

Demirci et al., "Single cell epitaxy by acoustic picolitre droplets," *Lab On A Chip*, 7(9):1139-1145, 2007.

Han et al., "A2780 human ovarian cancer cells with acquired paclitaxel resistance display cancer stem cell properties," *Oncol. Lett.*, 6:1295-1298, 2013.

International Preliminary Report on Patentability issued in corresponding PCT Application No. PCT/EP2016/074515, dated Apr. 17, 2018.

International Search Report and Written Opinion issued in corresponding PCT Application No. PCT/EP2016/074515, dated Nov. 16, 2018.

Peubez et al., "Antibiotic-free selection in *E. coli*: new considerations for optimal design and improved production," *Microb. Cell Fact.*, 9:65, 2010.

* cited by examiner

A)

B)

A

B

AUTOMATED METHOD FOR ISOLATION, SELECTION AND/OR DETECTION OF MICROORGANISMS OR CELLS COMPRISED IN A SOLUTION

This application is a national phase application under 35 U.S.C. § 371 of International Application No. PCT/EP2016/074515, filed Oct. 12, 2016, which claims benefit of International Application No. PCT/EP2015/073559, filed Oct. 12, 2015, the entire contents of each of which are hereby incorporated by reference.

FIELD OF THE INVENTION

The present invention relates to an automated method for obtaining at least one discrete colony from microorganisms or cells comprised in a solution, wherein said microorganisms or cells may comprise exogenous DNA, wherein said method includes the step of dispensing at least one defined volume of the solution comprising said microorganisms or cells onto a solid medium, which can in specific embodiments be a solid selective medium, using acoustic liquid transfer.

The present invention further relates to the use of an acoustic liquid transfer device for obtaining at least one discrete colony from microorganisms or cells comprised in a solution, wherein said microorganisms or cells may comprise exogenous DNA.

An automated method for determining the presence and/or quantity of microorganisms or cells potentially comprised in a solution is also part of the present invention. An acoustic liquid transfer device can also be used for such a determination.

BACKGROUND OF THE INVENTION

Transformation comprises the transfer of nucleic acids, most commonly plasmid DNA, into competent microorganisms, such as bacteria. Common transformation techniques comprise heat-shock transformation and electro-shock transformation. Transfection comprises the transfer of nucleic acids such as e.g. RNA or DNA into eukaryotic cells, such as e.g. human cells, insect cells or mouse cells.

For downstream analyses, it is essential to identify microorganisms (such as e.g. bacteria) or cells that i) comprise the transferred nucleic acid and ii) originate from a single transformant or transfectant and are thus genetically identical. A single transformant or transfectant is typically referred to as "colony forming unit" or "CFU".

In the following, a typical assay for obtaining a single transformant from a transformed bacterium and problems associated therewith will be outlined.

To account for item i) mentioned above, a selection based on a selection marker is typically employed, wherein a common selection marker is resistance to an antibiotic. Thus, the bacteria are plated on selective agar after the transformation, in the above situation containing an antibiotic, and only bacteria comprising the plasmid DNA are able to grow on this agar.

To account for item ii) mentioned above, dilution streaking is usually applied on a bench-scale in order to ensure that discrete colonies will be identifiable after incubation in at least a region of the plate. At low dilutions, overgrowth of the colonies is often observed, making such a region useless for further analyses since the corresponding colonies may not be genetically identical due to the overgrowth.

High throughput (HT) cloning, which is often robot-assisted parallel cloning of various different plasmid constructs, is increasingly used to generate cDNA libraries, BAC libraries, genomic DNA libraries, mutant libraries, or construct libraries. In the context of HT cloning, the handling of a transformation culture (containing an undefined number of transformants) to generate discrete colonies should be performed in an automated way, to save time, resources and labor costs. In HT cloning approaches, several transformation reactions (e.g. 6, 12, 24 or 96) are ideally handled in parallel, and only one culture plate or a multi well plate is ideally used to save time and resources.

There are commercially available, automated plating devices that are suitable for streaking or plating in a laboratory standard petri dish format. The following devices are based on streaking: PREVI® Isola (BioMerieux), Petri-Plater™ (Scirobotics) and InoqulA™ (BD Biosciences). There is also the option of relying on automatically generated serial dilutions and plating, e.g. the easySpiral Dilute® (Interscience). For all these options, there is a rather high risk of contamination and these options are not suitable for a high number of transformations or even different transformation reactions to be analyzed in parallel.

Thus, no automated method or device is known in the art that is suitable for obtaining discrete colonies in an economic manner while reducing the risk of contamination, which furthermore allows for an automated way of analyzing several transformations in parallel, as is the case e.g. in HT cloning.

The above applies accordingly for transfected eukaryotic cells, e.g. in therapeutic areas such as in particular in gene therapy.

There is also the need for analyzing in particular liquid biological samples or consumer products for the presence and/or quantity of microorganisms, in particular for the presence and/or quantity of pathogenic microorganisms.

Furthermore, for eukaryotic cells, there are also assays that are based on the formation of discrete colonies, e.g. the formation of stem cell colonies of progenitor stem cells from a stem cell suspension or when assessing whether eukaryotic cells, in particular cancer cells are capable of forming such discrete colonies and thus have stem cell-like properties.

Accordingly, there is the need for high-throughput methods for the analysis of liquid samples as regards the presence and/or quantity of microorganisms (in particular pathogenic microorganisms) or cells potentially comprised therein.

SUMMARY OF THE INVENTION

The present invention solves the above needs, inter alia by providing the methods as outlined in the first and fourth aspects of the invention. In the first aspect, the present invention relates to an automated method for obtaining at least one discrete colony from microorganisms or cells comprised in a solution. In the fourth aspect, the present invention relates to an automated method for determining the presence and/or quantity of microorganisms or cells potentially comprised in a solution, wherein the underlying basic principle is substantially identical to the principle employed in the afore-mentioned method of the first aspect of the invention. The present invention furthermore relates to the uses as indicated below in separate aspects.

In a first aspect, the present invention relates to an automated method for obtaining at least one discrete colony from microorganisms or cells comprised in a solution, the method comprising the steps of:

a) Providing a solution comprising microorganisms or cells;
b) Providing a solid medium suitable for growth of said microorganisms or cells;
c) Dispensing at least one defined volume of said solution provided in step a) onto said solid medium provided in step b) using acoustic liquid transfer; and
d) Incubating said solid medium under conditions suitable for growth of said microorganisms or cells and thus obtaining at least one discrete colony.

In a specific embodiment, the present invention relates to an automated method for obtaining at least one discrete colony from microorganisms or cells comprised in a solution, the method comprising the steps of:
a) Providing a solution comprising the microorganisms or cells;
b) Providing a solid medium suitable for growth of said microorganisms or cells;
c) Dispensing at least one defined volume of said solution provided in step a) onto said solid medium provided in step b) using acoustic liquid transfer; and
d) Incubating said solid medium under conditions suitable for growth of said microorganisms or cells and thus obtaining at least one discrete colony.

In a specific embodiment, discrete colonies are obtained by said method.

Said microorganisms or cells are capable of forming discrete colonies on a solid medium suitable for growth of the respective microorganisms or cells. Such microorganisms or cells are known to the skilled person and is it understood that the method of the first aspect is limited to the afore-mentioned microorganisms or cells.

In a specific embodiment, the microorganisms are selected from the group consisting of bacteria (e.g. *E. coli*), fungi (e.g. *S. cerevisiae*) and protists (e.g. xenic strains of *Acanthamoeba*).

When reference is made to protists herein, it can be preferred that said protist is generally selected from the group consisting of the Amoebozoa (e.g. Tubulinae, Flabellinea, *Stereomyxida*, Acanthamoebidae, *Entamoebida*, Mastigamoebidae or *Eumycetozoa*), Archaeplastida (e.g. *Glaucophyta*, Rhodophyceae or *Chloroplastida*), Chromalveolata (e.g. Cryptophyceae, *Haptophyta* or *Stramenopiles*), Exavata (e.g. *Fornicata, Parabasalia, Preaxostyla, Jakobida*, Heterolobosea or *Euglenozoa*), *Rhizaria* (e.g. *Cercozoa, Haplospodidia, Foraminifera* or *Radiolaria*), and *Opisthokonta* (e.g. *Mesomycetoza, Choanomonada* or *Metazoa*). It can be preferred that said protists are selected from the group consisting of *Chlorella; Chlamydomonas; Dunaliella; Haematococcus; Chorogonium; Scenedesmus; Euglena*; xenic strains of *Acanthamoeba, Naegleria, Hartmannella* and *Willaertia*; and xenic strains of *Vannella, Flabellula, Korotnevella, Paramoeba, Neoparamoeba, Platyamoeba* and *Vexillifera*.

In a specific embodiment, said cells are eukaryotic cells, preferably selected from the group consisting of human cells, insect cells and mouse cells. It can be particularly preferred that said cells are human cells including in particular human stem cells and human cancer cells.

In a specific embodiment, said solution comprising microorganisms or cells is liquid medium suitable for growth of said microorganisms or cells. For bacteria such as e.g. *E. coli*, such a liquid growth medium may e.g. be S.O.C. medium, SOB medium or LB medium as commonly known to the skilled person. For cells, in particular human or mouse cells, standard cell culture media such as BME, MEM, DMEM, GMEM, F10, F12, F12K, or RPMI-1649 (optionally complemented with serum) commonly known to the skilled person may be used.

In a specific embodiment, said solid medium is agar growth medium. For microorganisms such as e.g. *E. coli*, such solid medium may be LB agar as commonly known to the skilled person. For cells and in particular eukaryotic cells, such as e.g. stem cells, soft agar may be used. Such a soft agar may e.g. be 1% agarose in medium suitable for growth of the respective eukaryotic cells, which has been coated onto a suitable device (such as e.g. a multi-well plate) and allowed to cool.

Typical conditions suitable for growth of microorganisms are i) a temperature suitable for growth of the respective microorganisms (such as e.g. 30° C. or 37° C.), ii) aerobic or anaerobic conditions (usually aerobic conditions using breathing air with an oxygen content of about 21%), iii) a sufficient incubation period of usually several hours, e.g. 5 to 30 hours, 10 to 24 hours, or 15 to 20 hours, wherein about 16 hours can be particularly preferred, iv) a suitable humidity, such as e.g. regular humidity, etc. Such conditions are well known to the person skilled in the art and are applied according to the microorganisms used in the method of the first aspect. Such conditions can be found in standard text books.

Typical conditions suitable for growth of cells are i) a temperature suitable for growth of the respective cells (such as e.g. 37° C.), ii) aerobic or anaerobic conditions (usually aerobic conditions using breathing air with an oxygen content of about 21%), iii) a sufficient incubation period of usually several days, e.g. 1 to 10 days, 2 to 9 days, or 5 to 9 days, wherein about 6 to 8 days can be particularly preferred, iv) a suitable humidity, such as e.g. regular humidity, etc. Such conditions are well known to the person skilled in the art and are applied according to the cells used in the method of the first aspect. Such conditions can be found in standard text books.

In a preferred embodiment, said solution comprises an undefined number of colony-forming units.

In a particularly preferred embodiment, said acoustic liquid transfer is carried out by an acoustic liquid transfer device, preferably an Echo Liquid Handler or an ATS Acoustic Liquid Dispenser. The latter two devices are commercially available from the companies LabCyte Inc. (Echo Liquid Handler) and EDC Biosystems (ATS Acoustic Liquid Dispenser).

In a further particularly preferred embodiment, said method is carried out in parallel with at least two solutions comprising microorganisms or cells. It can further be preferred that said method is carried out on a multi-well plate. Alternatively, it can be preferred that said method is carried out on a plate containing a single well (e.g. Nunc™ OmniTray™). In a particularly preferred embodiment, the at least two solutions comprising microorganisms or cells are transferred via acoustic transfer onto distinct areas. Said setting is particularly advantageous in embodiments where automated picking of the obtained colonies is implemented. In view of the foregoing, in a further particularly preferred embodiment, said method is a high-throughput method. The method of the first aspect may thus also be referred to as automated, high throughput method.

In a specific particularly preferred embodiment, said method is carried out in parallel with at least two, three, four, five, six, seven, eight, or even more preferably with 12, 24, 48, 96 solutions comprising microorganisms or cells by using corresponding well plates (e.g., 12, 24, 48, 96). Alternatively, a plate containing a single well (e.g. Nunc™

OmniTray™) is used wherein cells are transferred onto 12, 24, 48, 96 distinct areas on the plate.

In a specific particularly preferred embodiment, said at least one discrete colony is isolated following step d), preferably by an automated high-throughput colony picker. Thus, the method of the first aspect may comprise a step e) following step d), namely wherein said at least one discrete colony is isolated.

In a specific embodiment, said at least one defined volume is selected from a range of from 1.0 nl to 100 µl; from a range of from 1.0 nl to 10 µl; from a range of from 2.5 nl to 1 µl; or from a range of from 2.5 nl to 100 nl. Said volume may e.g. be 1.0 nl, 2.5 nl, 5 nl, 7.5 nl, 10 nl, 15 nl, 20 nl, 25 nl, 30 nl, 35 nl, 40 nl, 45 nl, 50 nl, 58 nl, 60 nl, 70 nl, 80 nl, 90 nl, 100 nl, 110 nl, 115 nl, 122.5 nl, 130 nl, 140 nl, 150 nl, 160 nl, 170 nl, 180 nl, 190 nl, 200 nl, 205 nl, 210 nl, 220 nl, 230 nl, 240 nl, 250 nl, 260 nl, 270 nl, 280 nl, 285 nl, 300 nl, 350 nl, 400 nl, 450 nl, 500 nl, 520 nl, 540 nl, 572.5 nl, 600 nl, 700 nl, 800 nl, 900 nl, 1 µl, 1.5 µl, 2 µl, 2.5 µl, 3 µl, 4 µl, 5 µl, 6 µl, 7 ill, 8 µl, 9 µl or 10 µl. Said volume may preferably be 2.5 nl, 15 nl, 25 nl, 35 nl, 60 nl, 70 nl, 100 nl, 122.5 nl, 140 nl, 205 nl, 280 nl, 285 nl, 500 nl, 572.5 nl, 2 µl, or 10 µl.

In the following, four specific aspects 1A to 1D of the first aspect are described, wherein aspect 1A is most preferred, followed by aspect 1B, followed by aspect 1C, followed by aspect 1D. It is important to note that the afore-mentioned embodiments relating to the first aspect equally apply for the aspects 1A to 1D.

Aspect 1A of the First Aspect: Dispension of at Least Two Equally Defined Volumes in Step c)

In a preferred embodiment of the first aspect of the present invention, at least two equally defined volumes are dispensed in step c). Thus, in this embodiment, the method comprises the following steps:
  a) Providing a solution comprising microorganisms or cells;
  b) Providing a solid medium suitable for growth of said microorganisms or cells;
  c) Dispensing at least two equally defined volumes of said solution provided in step a) onto said solid medium provided in step b) using acoustic liquid transfer; and
  d) Incubating said solid medium under conditions suitable for growth of said microorganisms or cells and thus obtaining at least one discrete colony.

In this embodiment, it is preferred that a single solution comprising microorganisms or cells is provided in step a). Such a single solution can e.g. be the solution obtained after transformation/transduction of microorganisms or transfection/transduction of cells. Alternatively, such a single solution may be the result of a single dilution of said initial solution, e.g. a single solution directly obtained after transformation/transduction of microorganisms or transfection/transduction of cells.

As outlined above, said single solution comprising microorganisms or cells may be diluted by one dilution step, if this appears necessary (e.g. in view of a commonly known very high efficacy of transferring exogenous nucleic acid into said microorganisms or cells). Accordingly, in an embodiment, aspect 1A relates to a method comprising the steps of:
  a) Providing a solution comprising microorganisms or cells;
    1) Diluting said solution provided in step a); and
    2) Providing a diluted solution;
  b) Providing a solid medium suitable for growth of said microorganism or cells;
  c) Dispensing at least two equally defined volumes of said diluted solution provided in step a)2) onto said solid medium provided in step b) using acoustic liquid transfer; and
  d) Incubating said solid medium under conditions suitable for growth of said microorganisms or cells and thus obtaining at least one discrete colony.

In the above embodiment, a single diluted solution is preferably provided in step a)2). The single diluted solution may be the results of a dilution of 1:1000, 1:500, 1:400, 1:300, 1:200, 1:100, 1:50, 1:25, 1:20, 1:15, 1:10, 1:5, 1:2 or 1:1.5. Preferably, the dilution is carried out in the solution corresponding to the initial liquid carrier, e.g. liquid growth medium.

In a specific embodiment, said at least two equally defined volumes are selected from a range of from 1.0 nl to 100 µl; from a range of from 1.0 nl to 10 µl; from a range of from 2.5 nl to 1 µl; from a range of from 2.5 nl to 300 nl; from a range of from 10 nl to 200 nl; from a range of from 50 nl to 150 nl; or from a range of from 80 nl to 120 nl; It can be particularly preferred to use a defined volume of 95 nl.

In a preferred embodiment, more than two equally defined volumes are dispensed onto said solid medium provided in step b) using acoustic liquid transfer. It is also in this situation preferred that said more than two equally defined volumes are selected from a range of from 2.5 nl to 500 nl; from a range of from 2.5 nl to 300 nl; from a range of from 10 nl to 200 nl; from a range of from 50 nl to 150 nl; or from a range of from 80 nl to 120 nl; It can be particularly preferred to use a defined volume of 95 nl. It is also in this situation preferred to dispense 3 to 500, 10 to 100, or 50 to 100 equally defined volumes. It can be particularly preferred to dispense 64 equally defined volumes. It is also in this situation preferred that in total a volume of said solution comprising microorganisms or cells from a range of from 10 nl to 100 µl, from a range of from 100 nl to 50 µl, from a range of from 1 µl to 20 µl, from a range of from 2 µl to 15 µl, from a range of from 3 µl to 10 µl, from a range of from 3 µl to 8 µl, from a range of from 4 µl to 8 µl, or from a range of from 5 µl to 7 µl is dispensed onto said solid medium. It can be particularly preferred to dispense a total volume of 6.08 µl. It is also in this situation preferred that the total volume of said solution comprising microorganisms or cells dispensed onto said solid medium comprises between 1 to 200, 1 to 100, 1 to 80, 1 to 60, 1 to 50, 1 to 40, or 4 to 30, or 4 to 20 colony-forming units.

In a specific preferred embodiment, said at least two equally defined volumes are dispensed in a defined distance from each other. In an even preferred embodiment thereof, said defined distance is at least 100 µm. Depending on the volume to be used and if rather small volumes are used, said distance may, however, be less than 100 µm, such as e.g. 50 µm, 60 µm, 70 µm, 80 µm, or 90 µm. If rather large volume(s) are used, said defined distance may be at least 110 µm, 120 µm, 130 µm, 140 µm, 150 µm, 200 µm, 300 µm, 400 µm, 500 µm, 600 µm, 700 µm, 800 µm, 900 µm, 1000 µm, 1100 µm, 1200 µm, 1300 µm, 1400 µm, 1500 µm, 1600 µm or 1700 µm. It can be particularly preferred to use a defined distance of 1700 µm.

As outlined in the example section, it is possible to dispense equally defined volumes in a defined distance (FIG. 5).

Aspect 1B of the First Aspect: Dispension of at Least Two Differently Defined Volumes in Step c)

In a preferred embodiment of the first aspect of the present invention, at least two differently defined volumes are dispensed in step c). Thus, in this embodiment, the method comprises the following steps:
a) Providing a solution comprising microorganisms or cells;
b) Providing a solid medium suitable for growth of said microorganisms or cells;
c) Dispensing at least two differently defined volumes of said solution provided in step a) onto said solid medium provided in step b) using acoustic liquid transfer; and
d) Incubating said solid medium under conditions suitable for growth of said microorganisms or cells and thus obtaining at least one discrete colony.

In this embodiment, it is preferred that a single solution comprising microorganisms or cells is provided in step a). Such a single solution can e.g. be the solution obtained after transformation/transduction of microorganisms or transfection/transduction of cells. Alternatively, such a single solution may be the result of a single dilution of said initial solution, e.g. a single solution directly obtained after transformation/transduction of microorganisms or transfection/transduction of cells. This means that e.g. not several differently diluted solutions are provided, in which case it might be sufficient to dispense only a single defined volume of each of said differently diluted solutions (the corresponding embodiments relating thereto are described in aspect 1C). As outlined above, said single solution comprising microorganisms or cells may be diluted by one dilution step, if this appears necessary (e.g. in view of a commonly known very high efficacy of transferring exogenous nucleic acid into said microorganisms or cells). Accordingly, in an embodiment, aspect 1B relates to a method comprising the steps of:
a) Providing a solution comprising microorganisms or cells;
  1) Diluting said solution provided in step a); and
  2) Providing a diluted solution;
b) Providing a solid medium suitable for growth of said microorganism or cells;
c) Dispensing at least two differently defined volumes of said diluted solution provided in step a)2) onto said solid medium provided in step b) using acoustic liquid transfer; and
d) Incubating said solid medium under conditions suitable for growth of said microorganisms or cells and thus obtaining at least one discrete colony.

In the above embodiment, a single diluted solution is preferably provided in step a)2). The single diluted solution may be the results of a dilution of 1:1000, 1:500, 1:400, 1:300, 1:200, 1:100, 1:50, 1:25, 1:20, 1:15, 1:10, 1:5, 1:2 or 1:1.5. Preferably, the dilution is carried out in the solution corresponding to the initial liquid carrier, e.g. liquid growth medium.

In a specific embodiment, said at least two differently defined volumes are selected from a range of from 1.0 nl to 100 µl; from a range of from 1.0 nl to 10 µl; from a range of from 2.5 nl to 1 µl; or from a range of from 2.5 nl to 100 nl. For all these ranges, it is particularly preferred that one of said at least two differently defined volumes is selected near the lower end of said range, whereas the other of said at least two differently defined volumes is selected near the upper end of said range. Thus, it can be preferred that one volume is close to 1.0 nl, whereas the other volume is close to 100 µl, if the range is from 1.0 nl to 100 µl; one volume is close to 1.0 nl, whereas the other volume is close to 10 µl, if the range is from 1.0 nl to 10 µl; one volume is close to 2.5 nl, whereas the other volume is close to 1 µl, if the range is from 2.5 nl to 1 µl; or one volume is close to 2.5 nl, whereas the other volume is close to 100 nl, if the range is from 2.5 nl to 100 nl.

In a preferred embodiment, more than two differently defined volumes are dispensed onto said solid medium provided in step b) using acoustic liquid transfer. It is also in this situation preferred that said more than two differently defined volumes are selected from a range as outlined above, i.e. from a range of from 1.0 nl to 100 µl; from a range of from 1.0 nl to 10 µl; from a range of from 2.5 nl to 1 µl; or from a range of from 2.5 nl to 100 nl. It is of course again particularly preferred that the more than two differently defined volumes cover the range in a suitable manner, e.g. by separating the range in substantially about two equal parts if three differently defined volumes are used and two of them are still close to the (opposite) ends of the range. This correspondingly applies to a situation where four differently defined volumes are used (separation of the range in substantially about four equal parts). By adding more differently defined volumes, it is of course possible to cover the respective range in more discrete steps. It can be particularly preferred to dispense exactly or more than 3, 4, 5, 6, 7, 8, 9, 10, 15, 20, 40, 49, 50, 100, 520 differently defined volumes, which then even more preferably cover a range as defined above in discrete steps.

In a specific preferred embodiment, said at least two differently defined volumes are dispensed in a defined distance from each other. In an even preferred embodiment thereof, said defined distance is at least 100 µm. Depending on the volume(s) to be used and if rather small volumes are used, said distance may, however, be less than 100 µm, such as e.g. 50 µm, 60 µm, 70 µm, 80 µm, or 90 µm. If rather large volume(s) are used, said defined distance may be at least 110 µm, 120 µm, 130 µm, 140 µm, 150 µm, 200 µm, 300 µm, 400 µm, 500 µm, 600 µm, 700 µm, or 800 µm. It can be particularly preferred to use a defined distance of 800 µm.

As outlined in the example section, it is possible to dispense differently defined volumes in step c), wherein "a gradient" from the lowest to the highest volume is generated (see in particular FIGS. 1A and 2A). Using e.g. a linear dispensing pattern (as exemplary shown in FIG. 1A), it can be preferred to start at the lowest volume of 5 nl and to increase the volume by using defined volumes to the highest volume of 197.5 nl in linear increasing volumes using overall 520 differently defined volumes, each in a distance of 800 µm. Using e.g. a spiral dispensing pattern (as exemplary shown in FIG. 2A), it can be preferred to start at the lowest volume of 2.5 nl and to increase the volume by using defined volumes to the highest volume of either 15 nl, 25 nl, 35 nl or 70 nl in increasing volumes in a "spiral" pattern with the lowest volume in the inside of said spiral, each of the volumes in a distance of 800 µm. The latter dispensing pattern and similar patterns are particularly preferred.

Aspect 1C of the First Aspect: Provision of at Least Two Differently Diluted Solutions in Step a)

In an alternative approach to aspect 1B, aspect 1C relates to a method, wherein basically at least two different dilutions are provided prior to dispensing a defined volume onto a solid medium. Generally, the automatic generation of several dilutions is material- and thus cost-intense. There is generally also a higher risk of contaminations. Nevertheless, in some situations, the dilution-embodiments as disclosed in the following may be suitable. Accordingly, in an embodiment, aspect 1C relates to a method comprising the steps of:

a) Providing a solution comprising microorganisms or cells;
   1) Diluting said solution provided in step a); and
   2) Providing at least two differently diluted solutions;
b) Providing a solid medium suitable for growth of said microorganisms or cells;
c) Dispensing a defined volume of each of said at least two differently diluted solutions provided in step a)2) onto said solid medium provided in step b) using acoustic liquid transfer; and
d) Incubating said solid medium under conditions suitable for growth of microorganisms or cells and thus obtaining at least one discrete colony.

It is preferred in this embodiment that a single defined volume is dispensed in step c).

The at least two differently diluted solutions are preferably selected from a dilution range of from 1:1000 to 1:1.5; from a range of from 1:500 to 1:2; from a range of from 1:200 to 1:5; or from a range of from 1:100 to 1:10. For all these ranges, it is particularly preferred that one of said at least two differently diluted solutions is selected near the lower end of said range, whereas the other of said at least two differently diluted solution is selected near the upper end of said range. Thus, it can be preferred that one dilution is close to 1:1000, whereas the other dilution is close to 1:1.5, if the range is from 1:1000 to 1:1.5; one solution is close to 1:500, whereas the other dilution is close to 1:2, if the range is from 1:500 to 1:2; one dilution is close to 1:200, whereas the other dilution is close to 1:5, if the range is from 1:200 to 1:5; or one dilution is close to 1:100, whereas the other dilution is close to 1:10, if the range is from 1:100 to 1:10.

In a preferred embodiment, more than two differently diluted solutions are provided in step a)2). It is also in this situation preferred that said more than two differently diluted solutions are selected from a range as outlined above, i.e. from a range of from 1:1000 to 1:1.5; from a range of from 1:500 to 1:2; from a range of from 1:200 to 1:5; or from a range of from 1:100 to 1:10. It is of course again particularly preferred that the more than two differently diluted solutions cover the range in a suitable manner, e.g. by separating the range in substantially about two equal parts if three differently diluted solutions are used and two of them are still close to the (opposite) ends of the range. This correspondingly applies to a situation where four differently diluted solutions are used (separation of the range in substantially about four equal parts). By adding more differently diluted solutions, it is of course possible to cover the respective range in more discrete steps. It can be particularly preferred to provide exactly or more than 3, 4, 5, 6, 7, 8, 9, 10, 15, 20, 40, 49, 50, 100 differently diluted solutions in step a)2), which then even more preferably cover a range as defined above in discrete steps.

Thus, in a specific embodiment, at least three differently diluted solutions are provided in step a)2) and a single defined volume of each of said at least three differently diluted solutions is dispensed in step c). In a specific embodiment, at least four differently diluted solutions are provided in step a)2) and a single defined volume of each of said at least four differently diluted solutions is dispensed in step c).

In a specific embodiment relating to aspect 1B, said (preferably single) defined volume of each of said at least two differently diluted solutions is selected from a range of from 1.0 nl to 100 µl; from a range of from 1.0 nl to 10 µl; from a range of from 2.5 nl to 1 µl; or from a range of from 2.5 nl to 100 nl. Said volume may e.g. be 1.0 nl, 2.5 nl, 5 nl, 7.5 nl, 10 nl, 15 nl, 20 nl, 25 nl, 30 nl, 35 nl, 40 nl, 45 nl, 50 nl, 58 nl, 60 nl, 70 nl, 80 nl, 90 nl, 100 nl, 110 nl, 115 nl, 122.5 nl, 130 nl, 140 nl, 150 nl, 160 nl, 170 nl, 180 nl, 190 nl, 200 nl, 205 nl, 210 nl, 220 nl, 230 nl, 240 nl, 250 nl, 260 nl, 270 nl, 280 nl, 285 nl, 300 nl, 350 nl, 400 nl, 450 nl, 500 nl, 520 nl, 540 nl, 572.5 nl, 600 nl, 700 nl, 800 nl, 900 nl, 1 µl, 1.5 µl, 2 µl, 2.5 µl, 3 µl, 4 µl, 5 µl, 6 µl, 7 µl, 8 µl, 9 µl or 10 µl. Said volume may preferably be 2.5 nl, 15 nl, 25 nl, 35 nl, 60 nl, 70 nl, 100 nl, 122.5 nl, 140 nl, 205 nl, 280 nl, 285 nl, 500 nl, 572.5 nl, 2 µl, or 10 µl. Said volume may e.g. be 2.5 nl, 15 nl, 25 nl, 35 nl, 60 nl, 70 nl, 100 nl, 122.5 nl, 140 nl, 205 nl, 280 nl, 285 nl, 500 nl, 572.5 nl, 2,000 nl, or 10,000 nl. Preferred is a volume of 2.5 nl, 15 nl, 25 nl, 35 nl, 60 nl, 70 nl, 100 nl, 122.5 nl, 140 nl, 205 nl, 280 nl or 285 nl.

In a specific embodiment, said defined volumes of each of said at least two differently diluted solutions are dispensed in a defined distance from each other. In a preferred embodiment thereof, said defined distance is at least 100 µm. Depending on the volume(s) to be used and if rather small volumes are used, said distance may, however, be less than 100 µm, such as e.g. 50 µm, 60 µm, 70 µm, 80 µm, or 90 µm. If rather large volume(s) are used, said defined distance may be at least 110 µm, 120 µm, 130 µm, 140 µm, 150 µm, 200 µm, 300 µm, 400 µm, 500 µm, 600 µm, 700 µm, or 800 µm. It can be particularly preferred to use a defined distance of 800 µm.

Aspect 1D of the First Aspect: Provision of at Least Two Differently Diluted Solutions in Step a) and Dispension of at Least Two Differently Defined Volumes in Step c)

Aspect 1D relates to a method, wherein basically at least two different dilutions are provided prior to dispensing at least two differently defined volumes onto a solid medium. In some situations, the dilution-embodiments together with the dispension of at least two differently defined volumes as disclosed in the following may be suitable. Accordingly, in an embodiment, aspect 1D relates to a method comprising the steps of:

a) Providing a solution comprising microorganisms or cells;
   1) Diluting said solution provided in step a); and
   2) Providing at least two differently diluted solutions;
b) Providing a solid medium suitable for growth of said microorganisms or cells;
c) Dispensing at least two differently defined volumes of each of said at least two differently diluted solutions provided in step a)2) onto said solid medium provided in step b) using acoustic liquid transfer; and
d) Incubating said solid medium under conditions suitable for growth of microorganisms or cells and thus obtaining at least one discrete colony.

The at least two differently diluted solutions are preferably selected from a dilution range of from 1:1000 to 1:1.5; from a range of from 1:500 to 1:2; from a range of from 1:200 to 1:5; or from a range of from 1:100 to 1:10. For all these ranges, it is particularly preferred that one of said at least two differently diluted solutions is selected near the lower end of said range, whereas the other of said at least two differently diluted solution is selected near the upper end of said range. Thus, it can be preferred that one dilution is close to 1:1000, whereas the other dilution is close to 1:1.5, if the range is from 1:1000 to 1:1.5; one solution is close to 1:500, whereas the other dilution is close to 1:2, if the range is from 1:500 to 1:2; one dilution is close to 1:200, whereas the other dilution is close to 1:5, if the range is from 1:200 to 1:5; or one dilution is close to 1:100, whereas the other dilution is close to 1:10, if the range is from 1:100 to 1:10.

In a preferred embodiment, more than two differently diluted solutions are provided in step a)2). It is also in this situation preferred that said more than two differently diluted solutions are selected from a range as outlined above, i.e. from a range of from 1:1000 to 1:1.5; from a range of from 1:500 to 1:2; from a range of from 1:200 to 1:5; or from a range of from 1:100 to 1:10. It is of course again particularly preferred that the more than two differently diluted solutions cover the range in a suitable manner, e.g. by separating the range in substantially about two equal parts if three differently diluted solutions are used and two of them are still close to the (opposite) ends of the range. This correspondingly applies to a situation where four differently diluted solutions are used (separation of the range in substantially about four equal parts). By adding more differently diluted solutions, it is of course possible to cover the respective range in more discrete steps. It can be particularly preferred to provide exactly or more than 3, 4, 5, 6, 7, 8, 9, 10, 15, 20, 40, 49, 50, 100 differently diluted solutions in step a)2), which then even more preferably cover a range as defined above in discrete steps.

In a specific embodiment, said at least two differently defined volumes are selected from a range of from 1.0 nl to 100 μl; from a range of from 1.0 nl to 10 μl; from a range of from 2.5 nl to 1 μl; or from a range of from 2.5 nl to 100 nl. For all these ranges, it is particularly preferred that one of said at least two differently defined volumes is selected near the lower end of said range, whereas the other of said at least two differently defined volumes is selected near the upper end of said range. Thus, it can be preferred that one volume is close to 1.0 nl, whereas the other volume is close to 100 μl, if the range is from 1.0 nl to 100 μl; one volume is close to 1.0 nl, whereas the other volume is close to 10 μl, if the range is from 1.0 nl to 10 μl; one volume is close to 2.5 nl, whereas the other volume is close to 1 μl, if the range is from 2.5 nl to 1 μl; or one volume is close to 2.5 nl, whereas the other volume is close to 100 nl, if the range is from 2.5 nl to 100 nl.

In a preferred embodiment, more than two differently defined volumes are dispensed onto said solid medium provided in step b) using acoustic liquid transfer. It is also in this situation preferred that said more than two differently defined volumes are selected from a range as outlined above, i.e. from a range of from 1.0 nl to 100 μl; from a range of from 1.0 nl to 10 μl; from a range of from 2.5 nl to 1 μl; or from a range of from 2.5 nl to 100 nl. It is of course again particularly preferred that the more than two differently defined volumes cover the range in a suitable manner, e.g. by separating the range in substantially about two equal parts if three differently defined volumes are used and two of them are still close to the (opposite) ends of the range. This correspondingly applies to a situation where four differently defined volumes are used (separation of the range in substantially about four equal parts). By adding more differently defined volumes, it is of course possible to cover the respective range in more discrete steps. It can be particularly preferred to dispense exactly or more than 3, 4, 5, 6, 7, 8, 9, 10, 15, 20, 40, 49, 50, 100, 520 differently defined volumes, which then even more preferably cover a range as defined above in discrete steps.

The combination of the number of differently diluted solutions as well as the corresponding different dilution factors and the number of differently defined volumes depends on the individual situation. On a general level, it is noted that the number of differently defined volumes may be lower if more than one differently diluted solution is provided.

In a specific preferred embodiment, said at least two differently defined volumes are dispensed in a defined distance from each other. In an even preferred embodiment thereof, said defined distance is at least 100 μm. Depending on the volume(s) to be used and if rather small volumes are used, said distance may, however, be less than 100 μm, such as e.g. 50 μm, 60 μm, 70 μm, 80 μm, or 90 μm. If rather large volume(s) are used, said defined distance may be at least 110 μm, 120 μm, 130 μm, 140 μm, 150 μm, 200 μm, 300 μm, 400 μm, 500 μm, 600 μm, 700 μm, or 800 μm. It can be particularly preferred to use a defined distance of 800 μm.

As outlined in the example section, it is possible to dispense differently defined volumes in step c), wherein "a gradient" from the lowest to the highest volume is generated (see in particular FIGS. 1A and 2A). Using e.g. a linear dispensing pattern (as exemplary shown in FIG. 1A), it can be preferred to start at the lowest volume of 5 nl and to increase the volume by using defined volumes to the highest volume of 197.5 nl in linear increasing volumes using overall 520 differently defined volumes, each in a distance of 800 μm. Using e.g. a spiral dispensing pattern (as exemplary shown in FIG. 2A), it can be preferred to start at the lowest volume of 2.5 nl and to increase the volume by using defined volumes to the highest volume of either 15 nl, 25 nl, 35 nl or 70 nl in increasing volumes in a "spiral" pattern with the lowest volume in the inside of said spiral, each of the volumes in a distance of 800 μm. The latter dispensing pattern and similar patterns are particularly.

The following embodiments of aspect 1E relate to microorganisms or cells comprising exogenous nucleic acid.

Aspect 1E of the First Aspect: Method for Microorganisms and Cells Comprising Exogenous Nucleic Acids All of the above mentioned embodiments of the first aspect including aspects 1A, 1B, 1C and 1D also apply for aspect 1E, namely for an automated method for obtaining at least one discrete colony from microorganisms or cells comprising an exogenous nucleic acid. Accordingly, in an embodiment, aspect 1E relates to an automated method for obtaining at least one discrete colony from microorganisms or cells comprising an exogenous nucleic acid comprised in a solution, the method comprising the steps of:
  a) Providing a solution comprising microorganisms or cells comprising an exogenous nucleic acid;
  b) Providing a solid medium suitable for growth of said microorganisms or cells comprising an exogenous nucleic acid;
  c) Dispensing at least one defined volume of said solution provided in step a) onto said solid medium provided in step b) using acoustic liquid transfer; and
  d) Incubating said solid medium under conditions suitable for growth of said microorganisms or cells comprising an exogenous nucleic acid and thus obtaining at least one discrete colony.

It is again emphasized that all the afore-mentioned general embodiments relating to aspect 1 and all of the embodiments of aspect 1A, 1B, 1C and 1D also apply for the embodiment of aspect 1E. The embodiments of aspect 1A are of particular importance in this respect. Thus, it is particularly preferred that at least two equally defined volumes are dispensed in step c) of the method of present aspect 2. All specific embodiments thereof as mentioned above apply here as well. In specific situations, the embodiments of aspects 1B, 1C and 1D may, however, also apply.

In an embodiment specific to aspect 1E, said microorganisms comprising an exogenous nucleic acid are obtained by transforming microorganisms with said exogenous nucleic acid prior to step a). In an alternative embodiment thereof, said microorganisms comprising an exogenous nucleic acid are obtained by transducing microorganisms with said exogenous nucleic acid prior to step a). Such methods are known to the skilled person and alternative methods may be used to obtain microorganisms comprising an exogenous nucleic acid. In these embodiments, said solution comprises microorganisms comprising an exogenous nucleic acid and microorganisms not comprising an exogenous nucleic acid. This is because the efficacy of introducing exogenous nucleic acids is usually below 100%. As noted in the above embodiment "aspect 1E", the aim of this embodiment of the present invention resides therein to obtain at least one discrete colony from microorganisms comprising an exogenous nucleic acid.

In an embodiment specific to aspect 1E, said cells comprising an exogenous nucleic acid are obtained by transfecting or transducing cells with said exogenous nucleic acid prior to step a). These methods are well-known to the skilled person and alternative methods may be used to obtain cells comprising an exogenous nucleic acid. In these embodiments, said solution comprises cells comprising an exogenous nucleic acid and cells not comprising an exogenous nucleic acid. This is because the efficacy of introducing exogenous nucleic acids is usually below 100%. As noted in the above embodiment "aspect 1E", the aim of this embodiment of the present invention resides therein to obtain at least one discrete colony from cells comprising an exogenous nucleic acid.

In a specific embodiment, said exogenous nucleic acid is selected from the group consisting of DNA and RNA, wherein DNA is preferred. If DNA is used, said DNA is preferably selected from the group consisting of a DNA plasmid, a bacteriophage, a cosmid and an artificial chromosome. In a preferred embodiment, said exogenous nucleic acid is a DNA plasmid.

In a specific embodiment, said solution comprising microorganisms or cells comprising an exogenous nucleic acid is liquid medium not selective for microorganisms or cells comprising an exogenous nucleic acid but suitable for growth of said microorganisms or cells in general, i.e. also for microorganisms and cells not comprising an exogenous nucleic acid.

The following embodiments of aspect 1F relate to microorganisms or cells comprising exogenous nucleic acids in combination with a solid medium selective for growth of microorganisms or cells comprising an exogenous nucleic acid.

Aspect 1F of the First Aspect: Method for Microorganisms and Cells Comprising an Exogenous Nucleic Acid in Combination with a Solid Selective Medium In this specific embodiment, the solid medium provided in step b) is selective for growth of microorganisms or cells comprising an exogenous nucleic acid. It is immediately evident that this embodiment preferably applies in combination with the embodiment of aspect 1E.

Accordingly, in an embodiment, aspect 1F relates to an automated method for obtaining at least one discrete colony from microorganisms or cells comprising an exogenous nucleic acid comprised in a solution, the method comprising the steps of:
 a) Providing a solution comprising microorganisms or cells comprising an exogenous nucleic acid;
 b) Providing a solid medium selective for said microorganisms or cells comprising an exogenous nucleic acid;
 c) Dispensing at least one defined volume of said solution provided in step a) onto said solid medium provided in step b) using acoustic liquid transfer; and
 d) Incubating said solid medium under conditions suitable for growth of said microorganisms or cells comprising an exogenous nucleic acid and thus obtaining at least one discrete colony.

It is emphasized that all the afore-mentioned general embodiments relating to aspect 1 and all of the embodiments of aspect 1A, 1B, 1C and 1D also apply for the embodiment of aspect 1F. The embodiments of aspect 1A are of particular importance in this respect. Thus, it is particularly preferred that at least two equally defined volumes are dispensed in step c) of the method of present aspect 3. All specific embodiments thereof as mentioned above apply here as well. In specific situations, the embodiments of aspects 1B, 1C and 1D may, however, also apply.

In an embodiment specific to aspect 1F, said microorganisms comprising an exogenous nucleic acid are obtained by transforming microorganisms with said exogenous nucleic acid prior to step a). In an alternative embodiment thereof, said microorganisms comprising an exogenous nucleic acid are obtained by transducing microorganisms with said exogenous nucleic acid prior to step a). Such methods are known to the skilled person and alternative methods may be used to obtain microorganisms comprising an exogenous nucleic acid. In these embodiments, said solution comprises microorganisms comprising an exogenous nucleic acid and microorganisms not comprising an exogenous nucleic acid. This is because the efficacy of introducing exogenous nucleic acids is usually below 100%. As noted in the above embodiment "aspect 1F", the aim of this embodiment of the present invention resides therein to obtain at least one discrete colony from microorganisms comprising an exogenous nucleic acid. Accordingly, no colonies at all for microorganisms not comprising an exogenous nucleic acid should be obtained, or colonies of microorganisms comprising an exogenous nucleic acid and microorganisms not comprising an exogenous nucleic acid should be obtained and they can be distinguished from each other, e.g. by their colour (see below).

In an embodiment specific to aspect 1F, said cells comprising an exogenous nucleic acid are obtained by transfecting or transducing cells with said exogenous nucleic acid prior to step a). These methods are well-known to the skilled person and alternative methods may be used to obtain cells comprising an exogenous nucleic acid. In these embodiments, said solution comprises cells comprising an exogenous nucleic acid and cells not comprising an exogenous nucleic acid. This is because the efficacy of introducing exogenous nucleic acids is usually below 100%. As noted in the above embodiment "aspect 1F", the aim of this embodiment of the present invention resides therein to obtain at least one discrete colony from cells comprising an exogenous nucleic acid. Accordingly, no colonies at all for cells not comprising an exogenous nucleic acid should be obtained, or colonies of cells comprising an endogenous nucleic acid and colonies of cells not comprising an endogenous nucleic acid should be obtained and they can be distinguished from each other, e.g. by their colour (see below).

In a specific embodiment, said solution comprising microorganisms or cells comprising an exogenous nucleic acid is liquid medium not selective for microorganisms or cells comprising an exogenous nucleic acid but suitable for growth of said microorganisms or cells in general, i.e. also for microorganisms and cells not comprising an exogenous nucleic acid.

In a specific embodiment, said exogenous nucleic acid is selected from the group consisting of DNA and RNA, wherein DNA is preferred. If DNA is used, said DNA is preferably selected from the group consisting of a DNA plasmid, a bacteriophage, a cosmid and an artificial chromosome. In a preferred embodiment, said exogenous nucleic acid is a DNA plasmid.

Preferably, said exogenous nucleic acid encodes a selection marker. Even more preferably, said exogenous nucleic acid encodes a selection marker and said solid medium selective for microorganisms or cells comprising an exogenous nucleic acid is selective for expression of said selection marker in microorganisms or cells comprising said exogenous nucleic acid.

In a particularly preferred embodiment, said method is carried out in parallel with at least two solutions comprising microorganisms or cells comprising an exogenous nucleic acid. It is noted that said at least two solutions can of course differ with respect to the exogenous nucleic acid comprised in said microorganisms or cells, and this can be preferred for a high-throughput analysis. In another preferred embodiment, said at least two solutions differ with respect to the species of the microorganisms or the cell-type.

The following embodiments relate to selection systems that may be employed in the method of aspect 1F. It is noted that reference is made in the following mainly to DNA, in particular a DNA plasmid, and to microorganisms. This is to facilitate the understanding but is not to be regarded as limiting. Such systems may also be used with other types of nucleic acid as well as with cells, in particular eukaryotic cells, and are known to the skilled person.

It can be particularly preferred that said selection marker is a protein that confers resistance to an antibiotic, preferably to ampicillin and/or kanamycin. Alternatively, said selection marker allows for a colour distinction on said solid selective medium between microorganisms or cells comprising exogenous DNA and microorganisms or cells not comprising exogenous DNA, or between microorganisms or cells comprising a DNA plasmid without insert and microorganisms or cells comprising a DNA plasmid with insert. Such a selection marker is preferably β-galactosidase or a subunit or derivative thereof, which may allow for a blue-white selection on said solid medium and thus a colour distinction between colonies of microorganisms or cells comprising exogenous DNA and colonies of microorganisms or cells not comprising exogenous DNA.

In this context blue-white screening is a rapid and efficient technique for the identification of recombinant bacteria. It relies on the activity of β-galactosidase, an enzyme occurring in *E. coli*, which cleaves lactose into glucose and galactose. The presence of lactose in the surrounding environment triggers the lacZ operon in *E. coli*. The operon activity results in the production of β-galactosidase enzyme that metabolizes the lactose. Most plasmid vectors carry a short segment of lacZ gene that contains coding information for the first 146 amino acids of β-galactosidase. The host *E. coli* strains used are competent cells containing lacZΔM15 deletion mutation. When the plasmid is taken up by such cells, due to α-complementation process, a functional β-galatosidase enzyme is produced. The plasmids used in cloning are manipulated in such a way that this α-complementation process serves as a marker for recombination. A multiple cloning site (MCS) is present within the lacZ sequence in the plasmid. This sequence can be nicked by restriction enzymes to insert the foreign DNA. When a plasmid containing foreign DNA is taken up by the host *E. coli*, the α-complementation does not occur, therefore, a functional β-galactosidase enzyme is not produced. If the foreign DNA is not inserted into the plasmid or if it is inserted at a location other than MCS, the lacZ gene in the plasmid complements the lacZ deletion mutation in the host *E. coli* producing a functional enzyme. For screening the clones containing recombinant DNA, a chromogenic substrate known as X-gal is added to the agar plate. If β-galactosidase is produced, X-gal is hydrolyzed to form 5-bromo-4-chloro-indoxyl, which spontaneously dimerizes to produce an insoluble blue pigment called 5,5'-dibromo-4,4'-dichloro-indigo. The colonies formed by non-recombinant cells, therefore, appear blue in color while the recombinant ones appear white. The desired recombinant colonies can be easily identified as well as picked and cultured, if desired. Isopropyl β-D-1-thiogalactopyranoside (IPTG) is used along with X-gal for blue-white screening. IPTG is a non-metabolizable analog of galactose that induces the expression of lacZ gene. It should be noted that IPTG is not a substrate for β-galactosidase but only an inducer. For visual screening purposes, chromogenic substrate like X-gal is required.

As outlined in the following, said solid medium selective for microorganisms or cells comprising exogenous DNA will be adapted to the selection marker used in the method. Thus, if said selection marker is a protein that confers resistance to an antibiotic, said antibiotic is added to the solid medium. Thus, in this specific embodiment, an antibiotic such as e.g. ampicillin and/or kanamycin is comprised in concentrations routinely used for this purpose in the solid medium (e.g. 100 µg/ml ampicillin, or 50 µg/ml kanamycin). Alternatively, if e.g. the above-mentioned colour distinction is used and the selection marker is β-galactosidase or a subunit or derivative thereof, the solid medium will typically comprise in the routinely used concentrations i) a compound suitable for the induction of the β-galactosidase-gene, preferably Isopropyl-β-thiogalactopyranosid (IPTG) (e.g. 0.1 mM IPTG), and ii) a dye-substrate for the β-galactosidase or a subunit or derivative thereof, preferably X-Gal (e.g. 20 µg/ml X-Gal), that will be processed into the blue dye 5,5'-Dibromo-4,4'-Dichloro-Indigo.

In a particularly preferred embodiment said exogenous DNA encodes a selection marker which is a protein that confers resistance to an antibiotic, preferably to ampicillin and/or kanamycin and a selection marker that allows for a colour distinction on solid medium between microorganisms comprising a DNA plasmid without insert and microorganisms comprising a DNA plasmid with insert.

Finally, it is well known to the skilled person that the corresponding microorganisms used in the present method are also adapted to the selection system as outlined above. Thus, if the selection is e.g. based on resistance to antibiotics, such as e.g. ampicillin and/or kanamycin, the microorganisms not comprising said exogenous DNA will of course be sensitive to antibiotics and not grow on said solid medium selective for microorganisms comprising exogenous DNA. Likewise, if colour distinction should be used for selection, the corresponding microorganisms not comprising exogenous DNA will of course not comprise a gene encoding functional β-galactosidase. If colour distinction should be used for selection of microorganisms comprising a plasmid DNA with insert, the corresponding microorganisms will not express the encoded selection marker which therefore results in uncoloured (white) colonies. To the contrary, microorganisms comprising a plasmid DNA without insert will correspond to coloured (blue) colonies due to a functional expression of the encoded selection marker.

In other embodiments antibiotic-free selection is employed. Antibiotic-free strategies in *E. coli* are described e.g. in Peubez et al. Microbial Cell Factories 2010, 9:65.

In still other embodiments, post-segregational killing is used. Post-segregational killing is a mechanism by which DNA plasmids are stably maintained by expressing a gene product that would be toxic to cells becoming plasmid-free upon division. The most representative example of post-segregational killing of plasmid-free cells is the Hok/Sok system. The translation of the Hok (host killing) messenger, encoding a toxin lethal to the bacteria, is completely blocked by the anti-messenger Sok (suppression of killing). In the absence of plasmid, Sok, which is less stable than Hok, is lost first, allowing the translation of the Hok mRNA and expression of the toxin lethal to the cell.

In still other embodiments, essential gene complementation is used. The most common systems are briefly summarized in the following.

dapD: The most common way to achieve selection in the absence of antibiotics is via complementation of an essential gene making use of an expression plasmid in a strain with a defect or inhibited expression of the same essential gene. The dapD gene, which has a role in the Lysine biosynthetic pathway as well as cell wall assembly, has been selected, knowing that mutations in the dap pathway are lethal.

dapD and repressor titration: A more elaborated strategy still based on dapD is described and known to the skilled person, the so-called "operator repressor titration for antibiotic-free plasmid maintenance", proposed by Cobra Therapeutics. This is a model in which the plasmid loss induces the downregulation of the essential dapD gene, and thus bacterial death.

Translation initiation factor infA: As alternatives to dapD, other essential genes have been targeted for the same purpose, particularly infA coding for a translation initiation factor.

Amino-acid auxotrophy complementation: A proline-auxotrophic K12 strain obtained through chromosomal proBA gene deletion is described for the expression of antibody Fab fragment. In that particular case the plasmid-mediated complementation is used as a second selection mechanism to completely abolish plasmid loss during fermentation. According to the same principle an *E. coli* M15-derivated glycine-auxotrophic strain has been constructed and shown to produce comparable amounts of recombinant protein as a conventional system.

The murA gene and RNA/RNA interaction The expression of the essential gene murA encoding an enzyme essential for the biosynthesis of cell wall is under control of the Tet repressor, TetR expression is inhibited by an RNA-RNA antisense interaction with RNAI derived from plasmid origin of replication ColE1.

RNA-OUT based antibiotic-free selection system: A counter-selectable marker (sacB) levansucrase from *Bacillus subtilis*, under control of the RNA-IN promoter is integrated into the bacterial chromosome induces cell death in presence of sucrose. Plasmid maintenance is ensured by the presence of the plasmid-borne regulator RNA-OUT anti-messenger acting as a down regulator of the expression of levansucrase.

In still other embodiments, plasmid selection using an endogenous essential gene marker is used. The fabI-triclosan model system is based on the over-expression of a host essential gene in presence of a chemical inhibitor of its product.

In still other embodiments, mutual dependence is used. Thus, systems such as pCOR, are based on the complementation of an amber mutation.

In still other embodiments, poison/antidote selection is used. Thus, gene ccdB (the poison), is inserted into the bacterial genome and encodes a stable protein binding gyrase, an essential element for cell division. Upon binding gyrase, the ccdB gene product impairs DNA replication and induces cell death. Gene ccdA (the antidote), is plasmid-born and encodes an instable protein (90 amino acids) under control of the mob promoter, acting as a natural inhibitor of ccdB.

It is noted that the above embodiments relating to selection markers and corresponding media and agents are just exemplary. The skilled person knows that there are e.g. combinations of the above two embodiments or many other selection systems that can be used in the present method. It is clear to the skilled person in the present field that i) the microorganisms or cells, ii) a specific nucleic acid sequence comprised in said exogenous nucleic acid (such as e.g. a selection marker), and iii) the solid medium and compounds comprised therein, respectively, are adapted to one another and form a system of positively screening for microorganisms or cells comprising an exogenous nucleic acid (compared to microorganisms not comprising an exogenous nucleic acid) or for microorganisms or cells comprising an exogenous nucleic acid with an insert (compared to microorganisms or cells comprising an exogenous nucleic acid without an insert). The present invention does not add further selection methods. Rather, any selection method that has been or will be established for the purpose of distinguishing microorganisms or cells comprising an exogenous nucleic acid from microorganisms or cells not comprising an exogenous nucleic acid, or microorganisms or cells comprising an exogenous nucleic acid with insert from microorganisms or cells comprising an exogenous nucleic acid without an insert can be employed in the method according to this specific aspect of the present invention.

In a specific embodiment of aspect 1E, the microorganisms are selected from the group consisting of bacteria and fungi, wherein yeast is particularly preferred if fungi are selected. It can be preferred that said microorganisms are bacteria, wherein *Escherichia coli*, *Corynebacterium* (e.g. *Corynebacterium glutamicum*), *Pseudomonas fluorescens*, and *Streptomyces* (e.g. *Streptomyces lividans*) are particularly preferred. Most preferred can be *Escherichia coli* strains XL1-Blue, XL10-Gold, DH10B, DH5α, SURE, Stbl11-4, TOP10 and Mach1. Alternatively, said microorganisms are fungi, particularly yeasts, wherein *Arxula adeninivorans* (*Blastobotrys adeninivorans*), *Yarrowia lipolytica*, *Candida boidinii*, *Saccharomyces cerevisiae*, *Schizosaccharomyces pombe*, *Hansenula polymorpha* (*Pichia angusta*), *Pichia pastoris*, *Aspergillus* (e.g. *Aspergillus oryzae*), *Trichoderma* (e.g. *Trichoderma reesei*), and *Myceliophthora thermophila* are particularly preferred. Depending on the purpose, it can be most preferred to use *Saccharomyces cerevisiae* strains optimized for the analysis of interactions, such as e.g. yeast-two-hybrid-analyses. The above comments as regards the overall selection applied in the method of this aspect are of particular importance. As outlined above, at least part of the exogenous nucleic acid and the solid selective medium have to be chosen in accordance with the specific microorganism used.

In a specific embodiment of aspect 1F, said cells are eukaryotic cells and preferably selected from the group consisting of human cells, insect cells, monkey cells and mouse cells, wherein human stem cells, human cancer cells and mouse stem cells may be particularly preferred. The above comments as regards the overall selection applied in the method of this aspect are of particular importance. As outlined above, at least part of the exogenous nucleic acid and the solid selective medium have to be chosen in accordance with the specific cells used.

In a second aspect, the present invention relates to the use of acoustic liquid transfer and an acoustic liquid transfer device, respectively, for obtaining at least one discrete colony from microorganisms or cells comprised in a solution, wherein said microorganisms or cells may comprise an exogenous nucleic acid. Preferably, said acoustic liquid transfer device is an Echo Liquid Handler or an ATS Acoustic Liquid Dispenser.

In a preferred embodiment of the second aspect, the method according to the first aspect of the present invention including all embodiments is employed for obtaining said at least one discrete colony.

In a third aspect, the present invention relates to the use of acoustic liquid transfer and an acoustic liquid transfer device, respectively, in a method according to the first aspect of the present invention. Preferably, said acoustic liquid transfer device is an Echo Liquid Handler or an ATS Acoustic Liquid Dispenser.

In a fourth aspect, the present invention relates to an automated method for determining the presence and/or quantity of microorganisms or cells potentially comprised in a solution, the method comprising the steps of:
a) Providing a solution potentially comprising microorganisms or cells;
b) Providing a solid medium suitable for growth of said microorganisms or cells;
c) Dispensing at least one defined volume of said solution provided in step a) onto said solid medium provided in step b) using acoustic liquid transfer;
d) Incubating said solid medium under conditions suitable for growth of said microorganisms or cells and thus potentially obtaining colonies from said microorganisms or cells; and
e) Determining the presence and/or number of said potentially obtained colonies, wherein
  1) the presence of colonies indicates that said microorganisms or cells are present in said solution; and
  2) the number of colonies correlates with the quantity of said microorganisms or cells in said solution such that the number of colonies indicates the quantity of said microorganisms or cells in said solution.

In a specific embodiment, the present invention relates to an automated method for determining the presence and/or quantity of microorganisms or cells potentially comprised in a solution, the method comprising the steps of:
a) Providing the solution potentially comprising microorganisms or cells;
b) Providing a solid medium suitable for growth of said microorganisms or cells;
c) Dispensing at least one defined volume of said solution provided in step a) onto said solid medium provided in step b) using acoustic liquid transfer;
d) Incubating said solid medium under conditions suitable for growth of said microorganisms or cells and thus potentially obtaining colonies from said microorganisms or cells; and
e) Determining the presence and/or number of said potentially obtained colonies, wherein
  1) the presence of colonies indicates that said microorganisms or cells are present in said solution; and
  2) the number of colonies correlates with the quantity of said microorganisms or cells in said solution such that the number of colonies indicates the quantity of said microorganisms or cells in said solution.

Said microorganisms or cells potentially comprised in said solution are capable of forming discrete colonies on a solid medium suitable for growth of the respective microorganisms or cells. This will be outlined in more detail below.

In a specific embodiment, the microorganisms are selected from the group consisting of bacteria, fungi and protists. This will be outlined in more detail below.

In a specific embodiment, said cells are eukaryotic cells, preferably stem cells or cancer cells. Said stem cells can be selected from the group consisting of human stem cells, monkey stem cells and mouse stem cells. This will be outlined in more detail below.

In a specific embodiment, said solution potentially comprising microorganisms is a liquid sample, preferably a biological or cosmetic sample. This will be outlined in more detail below.

In a specific embodiment, said solution potentially comprising cells is liquid medium suitable for growth of said cells. For cells, in particular stem cells or cancer cells, standard cell culture media as described above (e.g. DMEM) commonly known to the skilled person may be used. This will be outlined in more detail below.

In a specific embodiment, said solid medium is agar growth medium. For microorganisms such as e.g. *E. coli*, such solid medium may be LB agar as commonly known to the skilled person. For cells and in particular eukaryotic cells, such as e.g. stem cells or cancer cells, soft agar may be used. Such a soft agar may e.g. be 1% agarose in the growth medium suitable for growth of the respective eukaryotic cells, which has been coated onto a suitable device (such as e.g. a multi-well plate) and allowed to cool.

Typical conditions suitable for growth of microorganisms are i) a temperature suitable for growth of the respective microorganisms (such as e.g. 30° C. or 37° C.), ii) aerobic or anaerobic conditions (usually aerobic conditions using breathing air with an oxygen content of about 21%), iii) a sufficient incubation period of usually several hours, e.g. 5 to 30 hours, 10 to 24 hours, or 15 to 20 hours, wherein about 16 hours can be particularly preferred, iv) a suitable humidity, such as e.g. regular humidity, etc. Such conditions are well known to the person skilled in the art and are applied according to the microorganisms used in the method of the first aspect. Such conditions can be found in standard text books.

Typical conditions suitable for growth of cells are i) a temperature suitable for growth of the respective cells (such as e.g. 37° C.), ii) aerobic or anaerobic conditions (usually aerobic conditions using breathing air with an oxygen content of about 21%), iii) a sufficient incubation period of usually several days, e.g. 1 to 10 days, 2 to 9 days, or 5 to 9 days, wherein about 6 to 8 days can be particularly preferred, iv) a suitable humidity, such as e.g. regular humidity, etc. Such conditions are well known to the person skilled in the art and are applied according to the cells used in the method of the first aspect. Such conditions can be found in standard text books.

In a particularly preferred embodiment, said acoustic liquid transfer is carried out by an acoustic liquid transfer device, preferably an Echo Liquid Handler or an ATS Acoustic Liquid Dispenser. The latter two devices are commercially available from the companies LabCyte Inc. (Echo Liquid Handler) and EDC Biosystems (ATS Acoustic Liquid Dispenser).

In a further particularly preferred embodiment, said method is carried out in parallel with at least two solutions potentially comprising microorganisms or cells. It can further be preferred that said method is carried out on a plate containing a single well. In view of the foregoing, in a further particularly preferred embodiment, said method is a high-throughput method. The method of the fourth aspect may thus also be referred to as automated, high throughput method.

In a specific particularly preferred embodiment, said potentially obtained colonies are determined in step e) by an automated device, preferably by taking a picture of the potential colonies and analyzing same using appropriate software.

In a specific embodiment, said at least one defined volume is selected from a range of from 1.0 nl to 100 µl; from a range of from 1.0 nl to 10 µl; from a range of from 2.5 nl to 1 µl; or from a range of from 2.5 nl to 100 nl. Said volume may e.g. be 1.0 nl, 2.5 nl, 5 nl, 7.5 nl, 10 nl, 15 nl, 20 nl, 25 nl, 30 nl, 35 nl, 40 nl, 45 nl, 50 nl, 58 nl, 60 nl, 70 nl, 80 nl, 90 nl, 100 nl, 110 nl, 115 nl, 122.5 nl, 130 nl, 140 nl, 150 nl, 160 nl, 170 nl, 180 nl, 190 nl, 200 nl, 205 nl, 210 nl, 220 nl, 230 nl, 240 nl, 250 nl, 260 nl, 270 nl, 280 nl, 285 nl, 300 nl, 350 nl, 400 nl, 450 nl, 500 nl, 520 nl, 540 nl, 572.5 nl, 600 nl, 700 nl, 800 nl, 900 nl, 1 µl, 1.5 µl, 2 µl, 2.5 µl, 3 µl, 4 µl, 5 µl, 6 µl, 7 µl, 8 µl, 9 µl or 10 µl. Said volume may preferably be 2.5 nl, 15 nl, 25 nl, 35 nl, 60 nl, 70 nl, 100 nl, 122.5 nl, 140 nl, 205 nl, 280 nl, 285 nl, 500 nl, 572.5 nl, 2 µl, or 10 µl.

In a specific embodiment, the present invention relates to an automated method for determining the presence of microorganisms or cells potentially comprised in a solution, the method comprising the steps of:
a) Providing a solution potentially comprising microorganisms or cells;
b) Providing a solid medium suitable for growth of said microorganisms or cells;
c) Dispensing at least one defined volume of said solution provided in step a) onto said solid medium provided in step b) using acoustic liquid transfer;
d) Incubating said solid medium under conditions suitable for growth of said microorganisms or cells and thus potentially obtaining colonies from said microorganisms or cells; and
e) Determining the presence of said potentially obtained colonies, wherein the presence of colonies indicates that said microorganisms or cells are present in said solution.

In a specific embodiment, the present invention relates to an automated method for determining the quantity of microorganisms or cells comprised in a solution, the method comprising the steps of:
a) Providing a solution comprising microorganisms or cells;
b) Providing a solid medium suitable for growth of said microorganisms or cells;
c) Dispensing at least one defined volume of said solution provided in step a) onto said solid medium provided in step b) using acoustic liquid transfer;
d) Incubating said solid medium under conditions suitable for growth of said microorganisms or cells and thus obtaining colonies from said microorganisms or cells; and
e) Determining the number of said obtained colonies, wherein the number of colonies correlates with the quantity of said microorganisms or cells in said solution such that the number of colonies indicates the quantity of said microorganisms or cells in said solution.

In a specific embodiment, the present invention relates to an automated method for determining the presence and quantity of microorganisms or cells potentially comprised in a solution, the method comprising the steps of:
a) Providing the solution potentially comprising microorganisms or cells;
b) Providing a solid medium suitable for growth of said microorganisms or cells;
c) Dispensing at least one defined volume of said solution provided in step a) onto said solid medium provided in step b) using acoustic liquid transfer;
d) Incubating said solid medium under conditions suitable for growth of said microorganisms or cells and thus potentially obtaining colonies from said microorganisms or cells; and
e) Determining the presence and number of said potentially obtained colonies, wherein
1) the presence of colonies indicates that said microorganisms or cells are present in said solution; and
2) the number of colonies correlates with the quantity of said microorganisms or cells in said solution such that the number of colonies indicates the quantity of said microorganisms or cells in said solution.

In the following, four specific aspects 4A to 4D are described, wherein aspect 4A is most preferred, followed by aspect 4B, followed by aspect 4C, followed by aspect 4D. It is important to note that the afore-mentioned embodiments relating to the fourth aspect equally apply for the aspects 4A to 4D.

Aspect 4A of the Fourth Aspect: Dispension of at Least Two Equally Defined Volumes in Step c)

In a preferred embodiment of the fourth aspect of the present invention, at least two equally defined volumes are dispensed in step c). Thus, in an embodiment, aspect 4A relates to a method comprising the following steps:
a) Providing a solution potentially comprising microorganisms or cells;
b) Providing a solid medium suitable for growth of said microorganisms or cells;
c) Dispensing at least two equally defined volumes of said solution provided in step a) onto said solid medium provided in step b) using acoustic liquid transfer;
d) Incubating said solid medium under conditions suitable for growth of said microorganisms or cells and thus potentially obtaining colonies from said microorganisms or cells; and
e) Determining the presence and/or number of said potentially obtained colonies, wherein
1) the presence of colonies indicates that said microorganisms or cells are present in said solution; and
2) the number of colonies correlates with the quantity of said microorganisms or cells in said solution such that the number of colonies indicates the quantity of said microorganisms or cells in said solution.

In this embodiment, it is preferred that a single solution potentially comprising microorganisms or cells is provided in step a). This means that e.g. not several differently diluted solution are provided, in which case it might be sufficient to dispense only a single defined volume of each of said differently diluted solutions. It is noted that said single solution potentially comprising microorganisms or cells may be diluted by one dilution step, if this appears necessary.

Accordingly, in an embodiment, aspect 4A relates to a method comprising the steps of:
a) Providing a solution potentially comprising microorganisms or cells;

1) Diluting said solution provided in step a); and
2) Providing a diluted solution;
b) Providing a solid medium suitable for growth of said microorganisms or cells;
c) Dispensing at least two equally defined volumes of said diluted solution provided in step a)2) onto said solid medium provided in step b) using acoustic liquid transfer;
d) Incubating said solid medium under conditions suitable for growth of said microorganisms or cells and thus potentially obtaining colonies from said microorganisms or cells; and
e) Determining the presence and/or number of said potentially obtained colonies, wherein
1) the presence of colonies indicates that said microorganisms or cells are present in said solution; and
2) the number of colonies correlates with the quantity of said microorganisms or cells in said solution such that the number of colonies indicates the quantity of said microorganisms or cells in said solution.

In the above embodiment, a single diluted solution is preferably provided in step a)2). The single diluted solution may be the results of a dilution of 1:1000, 1:500, 1:400, 1:300, 1:200, 1:100, 1:50, 1:25, 1:20, 1:15, 1:10, 1:5, 1:2 or 1:1.5.

In a specific embodiment, said at least two equally defined volumes are selected from a range of from 1.0 nl to 100 µl; from a range of from 1.0 nl to 10 µl; from a range of from 2.5 nl to 1 µl; from a range of from 2.5 nl to 300 nl; from a range of from 10 nl to 200 nl; from a range of from 50 nl to 150 nl; or from a range of from 80 nl to 120 nl; It can be particularly preferred to use a defined volume of 95 nl.

Aspect 4B of the Fourth Aspect: Dispension of at Least Two Differently Defined Volumes in Step c)

In a preferred embodiment of the fourth aspect of the present invention, at least two differently defined volumes are dispensed in step c). Thus, in an embodiment, aspect 4B relates to a method comprising the following steps:
a) Providing a solution potentially comprising microorganisms or cells;
b) Providing a solid medium suitable for growth of said microorganisms or cells;
c) Dispensing at least two differently defined volumes of said solution provided in step a) onto said solid medium provided in step b) using acoustic liquid transfer;
d) Incubating said solid medium under conditions suitable for growth of said microorganisms or cells and thus potentially obtaining colonies from said microorganisms or cells; and
e) Determining the presence and/or number of said potentially obtained colonies, wherein
1) the presence of colonies indicates that said microorganisms or cells are present in said solution; and
2) the number of colonies correlates with the quantity of said microorganisms or cells in said solution such that the number of colonies indicates the quantity of said microorganisms or cells in said solution.

In this embodiment, it is preferred that a single solution potentially comprising microorganisms or cells is provided in step a). This means that e.g. not several differently diluted solution are provided, in which case it might be sufficient to dispense only a single defined volume of each of said differently diluted solutions (the corresponding embodiments relating thereto are described in aspect 4C). It is noted that said single solution potentially comprising microorganisms or cells may be diluted by one dilution step, if this appears necessary. Accordingly, in an embodiment, aspect 4B relates to a method comprising the steps of:
a) Providing a solution potentially comprising microorganisms or cells;
1) Diluting said solution provided in step a); and
2) Providing a diluted solution;
b) Providing a solid medium suitable for growth of said microorganisms or cells;
c) Dispensing at least two differently defined volumes of said diluted solution provided in step a)2) onto said solid medium provided in step b) using acoustic liquid transfer;
d) Incubating said solid medium under conditions suitable for growth of said microorganisms or cells and thus potentially obtaining colonies from said microorganisms or cells; and
e) Determining the presence and/or number of said potentially obtained colonies, wherein
1) the presence of colonies indicates that said microorganisms or cells are present in said solution; and
2) the number of colonies correlates with the quantity of said microorganisms or cells in said solution such that the number of colonies indicates the quantity of said microorganisms or cells in said solution.

In the above embodiment, a single diluted solution is preferably provided in step a)2). The single diluted solution may be the results of a dilution of 1:1000, 1:500, 1:400, 1:300, 1:200, 1:100, 1:50, 1:25, 1:20, 1:15, 1:10, 1:5, 1:2 or 1:1.5.

In a specific embodiment, said at least two differently defined volumes are selected from a range of from 1.0 nl to 100 µl; from a range of from 1.0 nl to 10 µl; from a range of from 2.5 nl to 1 µl; or from a range of from 2.5 nl to 100 nl. For all these ranges, it is particularly preferred that one of said at least two differently defined volumes is selected near the lower end of said range, whereas the other of said at least two differently defined volumes is selected near the upper end of said range. Thus, it can be preferred that one volume is close to 1.0 nl, whereas the other volume is close to 100 µl, if the range is from 1.0 nl to 100 µl; one volume is close to 1.0 nl, whereas the other volume is close to 10 µl, if the range is from 1.0 nl to 10 µl; one volume is close to 2.5 nl, whereas the other volume is close to 1 µl, if the range is from 2.5 nl to 1 µl; or one volume is close to 2.5 nl, whereas the other volume is close to 100 nl, if the range is from 2.5 nl to 100 nl.

In a preferred embodiment, more than two differently defined volumes are dispensed onto said solid medium provided in step b) using acoustic liquid transfer. It is also in this situation preferred that said more than two differently defined volumes are selected from a range as outlined above, i.e. from a range of from 1.0 nl to 100 µl; from a range of from 1.0 nl to 10 µl; from a range of from 2.5 nl to 1 µl; or from a range of from 2.5 nl to 100 nl. It is of course again particularly preferred that the more than two differently defined volumes cover the range in a suitable manner, e.g. by separating the range in substantially about two equal parts if three differently defined volumes are used and two of them are still close to the (opposite) ends of the range. This correspondingly applies to a situation where four differently defined volumes are used (separation of the range in substantially about four equal parts). By adding more differently defined volumes, it is of course possible to cover the respective range in more discrete steps. It can be particularly preferred to dispense exactly or more than 3, 4, 5, 6, 7, 8, 9, 10, 15, 20, 40, 49, 50, 100, 520 differently defined volumes, which then even more preferably cover a range as defined above in discrete steps.

In a specific preferred embodiment, said at least two differently defined volumes are dispensed in a defined distance from each other. In an even preferred embodiment thereof, said defined distance is at least 100 µm. Depending on the volume(s) to be used and if rather small volumes are used, said distance may, however, be less than 100 µm, such as e.g. 50 µm, 60 µm, 70 µm, 80 µm, or 90 µm. If rather large volume(s) are used, said defined distance may be at least 110 µm, 120 µm, 130 µm, 140 µm, 150 µm, 200 µm, 300 µm, 400 µm, 500 µm, 600 µm, 700 µm, or 800 µm. It can be particularly preferred to use a defined distance of 800 µm.

As outlined in the example section, it is possible to dispense differently defined volumes in step c), wherein "a gradient" from the lowest to the highest volume is generated (see in particular FIGS. 1A and 2A). Using e.g. a linear dispensing pattern (as exemplary shown in FIG. 1A), it can be preferred to start at the lowest volume of 5 nl and to increase the volume by using defined volumes to the highest volume of 197.5 nl in linear increasing volumes using overall 520 differently defined volumes, each in a distance of 800 µm. Using e.g. a spiral dispensing pattern (as exemplary shown in FIG. 2A), it can be preferred to start at the lowest volume of 2.5 nl and to increase the volume by using defined volumes to the highest volume of either 15 nl, 25 nl, 35 nl or 70 nl in increasing volumes in a "spiral" pattern with the lowest volume in the inside of said spiral, each of the volumes in a distance of 800 µm. The latter dispensing pattern and similar patterns are particularly preferred.

Aspect 4C of the Fourth Aspect: Provision of at Least Two Differently Diluted Solutions in Step a)

In an alternative approach to aspect 4B, aspect 4C relates to a method, wherein basically at least two different dilutions are provided prior to dispensing a defined volume onto a solid medium. Generally, the automatic generation of several dilutions is material- and thus cost-intense. There is generally also a higher risk of contaminations. Nevertheless, in some situations, the dilution-embodiments as disclosed in the following may be suitable. Accordingly, in an embodiment, aspect 4C relates to a method comprising the steps of:
  a) Providing a solution potentially comprising microorganisms or cells;
    1) Diluting said solution provided in step a); and
    2) Providing at least two differently diluted solutions;
  b) Providing a solid medium suitable for growth of said microorganisms or cells;
  c) Dispensing a defined volume of each of said at least two differently diluted solutions provided in step a)2) onto said solid medium provided in step b) using acoustic liquid transfer;
  d) Incubating said solid medium under conditions suitable for growth of said microorganisms or cells and thus potentially obtaining colonies from said microorganisms or cells; and
  e) Determining the presence and/or number of said potentially obtained colonies, wherein
    1) the presence of colonies indicates that said microorganisms or cells are present in said solution; and
    2) the number of colonies correlates with the quantity of said microorganisms or cells in said solution such that the number of colonies indicates the quantity of said microorganisms or cells in said solution.

It is preferred in this embodiment that a single defined volume is dispensed in step c).

The at least two differently diluted solutions are preferably selected from a dilution range of from 1:1000 to 1:1.5; from a range of from 1:500 to 1:2; from a range of from 1:200 to 1:5; or from a range of from 1:100 to 1:10. For all these ranges, it is particularly preferred that one of said at least two differently diluted solutions is selected near the lower end of said range, whereas the other of said at least two differently diluted solution is selected near the upper end of said range. Thus, it can be preferred that one dilution is close to 1:1000, whereas the other dilution is close to 1:1.5, if the range is from 1:1000 to 1:1.5; one solution is close to 1:500, whereas the other dilution is close to 1:2, if the range is from 1:500 to 1:2; one dilution is close to 1:200, whereas the other dilution is close to 1:5, if the range is from 1:200 to 1:5; or one dilution is close to 1:100, whereas the other dilution is close to 1:10, if the range is from 1:100 to 1:10.

In a preferred embodiment, more than two differently diluted solutions are provided in step a)2). It is also in this situation preferred that said more than two differently diluted solutions are selected from a range as outlined above, i.e. from a range of from 1:1000 to 1:1.5; from a range of from 1:500 to 1:2; from a range of from 1:200 to 1:5; or from a range of from 1:100 to 1:10. It is of course again particularly preferred that the more than two differently diluted solutions cover the range in a suitable manner, e.g. by separating the range in substantially about two equal parts if three differently diluted solutions are used and two of them are still close to the (opposite) ends of the range. This correspondingly applies to a situation where four differently diluted solutions are used (separation of the range in substantially about four equal parts). By adding more differently diluted solutions, it is of course possible to cover the respective range in more discrete steps. It can be particularly preferred to provide exactly or more than 3, 4, 5, 6, 7, 8, 9, 10, 15, 20, 40, 49, 50, 100 differently diluted solutions in step a)2), which then even more preferably cover a range as defined above in discrete steps.

Thus, in a specific embodiment, at least three differently diluted solutions are provided in step a)2) and a single defined volume of each of said at least three differently diluted solutions is dispensed in step c). In a specific embodiment, at least four differently diluted solutions are provided in step a)2) and a single defined volume of each of said at least four differently diluted solutions is dispensed in step c).

In a specific embodiment relating to aspect 4C, said (preferably single) defined volume of each of said at least two differently diluted solutions is selected from a range of from 1.0 nl to 100 µl; from a range of from 1.0 nl to 10 µl; from a range of from 2.5 nl to 1 µl; or from a range of from 2.5 nl to 100 nl. Said volume may e.g. be 1.0 nl, 2.5 nl, 5 nl, 7.5 nl, 10 nl, 15 nl, 20 nl, 25 nl, 30 nl, 35 nl, 40 nl, 45 nl, 50 nl, 58 nl, 60 nl, 70 nl, 80 nl, 90 nl, 100 nl, 110 nl, 115 nl, 122.5 nl, 130 nl, 140 nl, 150 nl, 160 nl, 170 nl, 180 nl, 190 nl, 200 nl, 205 nl, 210 nl, 220 nl, 230 nl, 240 nl, 250 nl, 260 nl, 270 nl, 280 nl, 285 nl, 300 nl, 350 nl, 400 nl, 450 nl, 500 nl, 520 nl, 540 nl, 572.5 nl, 600 nl, 700 nl, 800 nl, 900 nl, 1 µl, 1.5 µl, 2 µl, 2.5 µl, 3 µl, 4 µl, 5 µl, 6 µl, 7 µl, 8 µl, 9 µl or 10 µl. Said volume may preferably be 2.5 nl, 15 nl, 25 nl, 35 nl, 60 nl, 70 nl, 100 nl, 122.5 nl, 140 nl, 205 nl, 280 nl, 285 nl, 500 nl, 572.5 nl, 2 µl, or 10 µl. Said volume may e.g. be 2.5 nl, 15 nl, 25 nl, 35 nl, 60 nl, 70 nl, 100 nl, 122.5 nl, 140 nl, 205 nl, 280 nl, 285 nl, 500 nl, 572.5 nl, 2,000 nl, or 10,000 nl. Preferred is a volume of 2.5 nl, 15 nl, 25 nl, 35 nl, 60 nl, 70 nl, 100 nl, 122.5 nl, 140 nl, 205 nl, 280 nl or 285 nl.

In a specific embodiment, said defined volumes of each of said at least two differently diluted solutions are dispensed in a defined distance from each other. In a preferred embodiment thereof, said defined distance is at least 100 µm. Depending on the volume(s) to be used and if rather small volumes are used, said distance may, however, be less than 100 µm, such as e.g. 50 µm, 60 µm, 70 µm, 80 µm, or 90 µm. If rather large volume(s) are used, said defined distance may be at least 110 µm, 120 µm, 130 µm, 140 µm, 150 µm, 200 µm, 300 µm, 400 µm, 500 µm, 600 µm, 700 µm, or 800 µm. It can be particularly preferred to use a defined distance of 800 µm.

Aspect 4D of the Fourth Aspect: Provision of at Least Two Differently Diluted Solutions in Step a) and Dispension of at Least Two Differently Defined Volumes in Step c)

Aspect 4D relates to a method, wherein basically at least two different dilutions are provided prior to dispensing at least two differently defined volumes onto a solid medium. In some situations, the dilution-embodiments together with the dispension of at least two differently defined volumes as disclosed in the following may be suitable. Accordingly, in an embodiment, aspect 4D relates to a method comprising the steps of:
  a) Providing a solution potentially comprising microorganisms or cells;
    1) Diluting said solution provided in step a); and
    2) Providing at least two differently diluted solutions;
  b) Providing a solid medium suitable for growth of said microorganisms or cells;
  c) Dispensing at least two differently defined volumes of each of said at least two differently diluted solutions provided in step a)2) onto said solid medium provided in step b) using acoustic liquid transfer;
  d) Incubating said solid medium under conditions suitable for growth of said microorganisms or cells and thus potentially obtaining colonies from said microorganisms or cells; and
  e) Determining the presence and/or number of said potentially obtained colonies, wherein
    1) the presence of colonies indicates that said microorganisms or cells are present in said solution; and
    2) the number of colonies correlates with the quantity of said microorganisms or cells in said solution such that the number of colonies indicates the quantity of said microorganisms or cells in said solution.

The at least two differently diluted solutions are preferably selected from a dilution range of from 1:1000 to 1:1.5; from a range of from 1:500 to 1:2; from a range of from 1:200 to 1:5; or from a range of from 1:100 to 1:10. For all these ranges, it is particularly preferred that one of said at least two differently diluted solutions is selected near the lower end of said range, whereas the other of said at least two differently diluted solution is selected near the upper end of said range. Thus, it can be preferred that one dilution is close to 1:1000, whereas the other dilution is close to 1:1.5, if the range is from 1:1000 to 1:1.5; one solution is close to 1:500, whereas the other dilution is close to 1:2, if the range is from 1:500 to 1:2; one dilution is close to 1:200, whereas the other dilution is close to 1:5, if the range is from 1:200 to 1:5; or one dilution is close to 1:100, whereas the other dilution is close to 1:10, if the range is from 1:100 to 1:10.

In a preferred embodiment, more than two differently diluted solutions are provided in step a)2). It is also in this situation preferred that said more than two differently diluted solutions are selected from a range as outlined above, i.e. from a range of from 1:1000 to 1:1.5; from a range of from 1:500 to 1:2; from a range of from 1:200 to 1:5; or from a range of from 1:100 to 1:10. It is of course again particularly preferred that the more than two differently diluted solutions cover the range in a suitable manner, e.g. by separating the range in substantially about two equal parts if three differently diluted solutions are used and two of them are still close to the (opposite) ends of the range. This correspondingly applies to a situation where four differently diluted solutions are used (separation of the range in substantially about four equal parts). By adding more differently diluted solutions, it is of course possible to cover the respective range in more discrete steps. It can be particularly preferred to provide exactly or more than 3, 4, 5, 6, 7, 8, 9, 10, 15, 20, 40, 49, 50, 100 differently diluted solutions in step a)2), which then even more preferably cover a range as defined above in discrete steps.

In a specific embodiment, said at least two differently defined volumes are selected from a range of from 1.0 nl to 100 µl; from a range of from 1.0 nl to 10 µl; from a range of from 2.5 nl to 1 µl; or from a range of from 2.5 nl to 100 nl. For all these ranges, it is particularly preferred that one of said at least two differently defined volumes is selected near the lower end of said range, whereas the other of said at least two differently defined volumes is selected near the upper end of said range. Thus, it can be preferred that one volume is close to 1.0 nl, whereas the other volume is close to 100 µl, if the range is from 1.0 nl to 100 µl; one volume is close to 1.0 nl, whereas the other volume is close to 10 µl, if the range is from 1.0 nl to 10 µl; one volume is close to 2.5 nl, whereas the other volume is close to 1 µl, if the range is from 2.5 nl to 1 µl; or one volume is close to 2.5 nl, whereas the other volume is close to 100 nl, if the range is from 2.5 nl to 100 nl.

In a preferred embodiment, more than two differently defined volumes are dispensed onto said solid medium provided in step b) using acoustic liquid transfer. It is also in this situation preferred that said more than two differently defined volumes are selected from a range as outlined above, i.e. from a range of from 1.0 nl to 100 µl; from a range of from 1.0 nl to 10 µl; from a range of from 2.5 nl to 1 µl; or from a range of from 2.5 nl to 100 nl. It is of course again particularly preferred that the more than two differently defined volumes cover the range in a suitable manner, e.g. by separating the range in substantially about two equal parts if three differently defined volumes are used and two of them are still close to the (opposite) ends of the range. This correspondingly applies to a situation where four differently defined volumes are used (separation of the range in substantially about four equal parts). By adding more differently defined volumes, it is of course possible to cover the respective range in more discrete steps. It can be particularly preferred to dispense exactly or more than 3, 4, 5, 6, 7, 8, 9, 10, 15, 20, 40, 49, 50, 100, 520 differently defined volumes, which then even more preferably cover a range as defined above in discrete steps.

The combination of the number of differently diluted solutions as well as the corresponding different dilution factors and the number of differently defined volumes depends on the individual situation. On a general level, it is noted that the number of differently defined volumes may be lower if more than one differently diluted solution is provided.

In a specific preferred embodiment, said at least two differently defined volumes are dispensed in a defined distance from each other. In an even preferred embodiment thereof, said defined distance is at least 100 µm. Depending on the volume(s) to be used and if rather small volumes are used, said distance may, however, be less than 100 µm, such as e.g. 50 µm, 60 µm, 70 µm, 80 µm, or 90 µm. If rather large volume(s) are used, said defined distance may be at least 110 µm, 120 µm, 130 µm, 140 µm, 150 µm, 200 µm, 300 µm, 400 µm, 500 µm, 600 µm, 700 µm, or 800 µm. It can be particularly preferred to use a defined distance of 800 µm.

As outlined in the example section, it is possible to dispense differently defined volumes in step c), wherein "a gradient" from the lowest to the highest volume is generated (see in particular FIGS. 1A and 2A). Using e.g. a linear dispensing pattern (as exemplary shown in FIG. 1A), it can be preferred to start at the lowest volume of 5 nl and to increase the volume by using defined volumes to the highest volume of 197.5 nl in linear increasing volumes using overall 520 differently defined volumes, each in a distance of 800 µm. Using e.g. a spiral dispensing pattern (as exemplary shown in FIG. 2A), it can be preferred to start at the lowest volume of 2.5 nl and to increase the volume by using defined volumes to the highest volume of either 15 nl, 25 nl, 35 nl or 70 nl in increasing volumes in a "spiral" pattern with the lowest volume in the inside of said spiral, each of the volumes in a distance of 800 µm. The latter dispensing pattern and similar patterns are particularly.

Aspect 4E of the Fourth Aspect: Presence and/or Quantity of Microorganisms Potentially Comprised in a Solution The basic situation underlying aspect 4E is that a liquid sample is provided and that it is not known whether said sample comprises microorganisms, in particular pathogenic microorganisms. The method of aspect 4E is capable of determining whether such microorganisms are present in said liquid sample. There may also be the situation that it has been generally determined that specific microorganisms, in particular pathogenic microorganisms, are present in a liquid sample, but the quantity of said microorganisms in said sample is not known. The method of aspect 4E is also capable of determining the quantity of such microorganisms in said liquid sample.

In an embodiment, aspect 4E thus relates to a method for determining the presence and/or quantity of microorganisms potentially comprised in a solution, wherein the method comprises the steps of:
a) Providing a liquid sample potentially comprising microorganisms;
b) Providing a solid medium suitable for growth of said microorganisms;
c) Dispensing at least one defined volume of said liquid sample provided in step a) onto said solid medium provided in step b) using acoustic liquid transfer;
d) Incubating said solid medium under conditions suitable for growth of said microorganisms and thus potentially obtaining colonies from said microorganisms; and
e) Determining the presence and/or number of said potentially obtained colonies, wherein
  1) the presence of colonies indicates that said microorganisms are present in said liquid sample; and
  2) the number of colonies correlates with the quantity of said microorganisms in said liquid sample such that the number of colonies indicates the quantity of said microorganisms in said liquid sample.

All of the above mentioned embodiments of the fourth aspect including aspects 4A, 4B, 4C and 4D also apply for aspect 4E.

In a particularly preferred embodiment, said liquid sample is derived from a human being or an animal, e.g. blood, urine, saliva or cerebrospinal fluid. In another particularly preferred embodiment, said liquid sample is water, waste water, food, a pharmaceutical product or a cosmetical product. In general, the liquid sample may be any sample, where the presence and/or quantity of microorganisms have to be detected.

It is clear from the above that the microorganisms that can be analyzed in the present method are microorganisms that are capable of forming colonies on a solid medium suitable for growth of the microorganisms. Generally, there is no limitation as regards such microorganisms as long as the required solid medium suitable for growth and conditions suitable for growth are known. This is the case for all microorganisms outlined in the following, and corresponding solid media and growth conditions are known to the skilled person and can be found in standard text books.

In a preferred embodiment, said microorganisms are selected from bacteria, fungi and single-celled eukaryotes. A particularly relevant embodiment of the fourth aspect relates to pathogenic microorganisms. Exemplary pathogenic microorganisms that are within the scope of this embodiment are listed in the following. This is not to be regarded as limiting.

Pathogenic Bacteria: *Bacillus* (e.g. *Bacillus anthracis, Bacillus cereus*); *Bartonella* (e.g. *Bartonella henselae, Bartonella quintana*); *Bordetella* (e.g. *Bordetella pertussis*); *Borrelia* (e.g. *Borrelia burgdoferri, Borrelia garinii, Borrelia afzelii, Borrelia recurrentis*); *Brucella* (e.g. *Brucella abortus, Brucella canis, Brucella melitensis, Brucella suis*); *Campylobacter* (e.g. *Campylobacter jejuni*); *Chlamydia* and *Chlamydophila* (e.g. *Chlamydia pneumoniae, Chlamydia trachomatis, Chlamydophila psittaci*); *Clostridium* (e.g. *Chlostridium botulinum, Clostridium difficile, Clostridium perfringens, Clostdridium tetani*); *Corynebacterium* (e.g. *Corynebacterium diphtheriae*); *Enterococcus* (e.g. *Enterococcus faecalis, Enterococcus faecium*); *Escherichia* (e.g. *Escherichia coli*); *Francisella* (e.g. *Francisella tularensis*); *Haemophilus* (e.g. *Haemophilus influenzae*); *Heliobacter* (e.g. *Heliobacter pylori*); *Legionella* (e.g. *Legionella pneumophila*); *Leptospira* (e.g. *Leptospira interrogans, Leptospira santarosai, Leptospira weilii, Leptospira noguchii*); *Listeria* (e.g. *Listeria monocytogenes*); *Mycobacterium* (e.g. *Mycobacterium leprae, Mycobacterium tuberculosis, Mycobacterium ulcerans*); *Mycoplasma* (e.g. *Mycoplasma pneumoniae*); *Neisseria* (e.g. *Neisseria gonorrhoeae, Neisseria meningitidis*); *Pseudomonas* (*Pseudomonas areuginosa*); *Rickettsia* (*Rickettsia rickettsii*); *Salmonella* (*Salmonella typhi, Salmonella typhimurium*); *Shigella* (e.g. *Shigella sonnei*); *Staphylococcus* (e.g. *Staphylococcus aureus, Staphylococcus epidermidis, Staphylococcus saprophyticus*); *Streptococcus* (e.g. *Streptococcus agalactiae, Streptococcus pneumoniae, Streptococcus pyogenes*); *Treponema* (e.g. *Treponema pallidum*); *Ureaplasma* (e.g. *Ureaplasma urealyticum*); *Vibrio* (e.g. *Vibrio cholerae*); *Yersinia* (e.g. *Yersinia pestis, Yersinia enterocolitica, Yersinia pseudotuberculosis*).

Pathogenic Fungi: *Candida* (e.g. *Candida* species); *Aspergillus* (e.g. *Aspergillus fumigatus, Aspergillus flavus, Aspergillus clavatus*); *Cryptococcus* (e.g. *Cryptococcus neoformans, Cryptococcus laurentii, Cryptococcus albidus, Cryptococcus gattii*); *Histoplasma* (e.g. *Histoplasma capsulatum*); *Stachybotrys* (e.g. *Stachybotrys chartarum*).

Also encompassed is a "mold fungus" (referred to as "mold" in the following): A mold is a fungus that grows in the form of multicellular filaments called hyphae. In contrast, fungi that can adopt a single celled growth habit are called yeasts. Molds are a large and taxonomically diverse number of fungal species where the growth of hyphae results in discoloration and a fuzzy appearance, especially on food.

The network of these tubular branching hyphae, called a mycelium, is considered a single organism.

Further relevant fungi are: *Acremonium, Dematiaceae, Phoma, Alternaria, Eurotium, Rhizopus, Aspergillus, Fusarium, Scopulariopsis, Aureobasidium, Monilia, Stachybotrys, Botrytis, Mucor, Stemphylium, Chaetomium, Mycelia sterilia, Trichoderma, Cladosporium, Neurospora, Ulocladium, Paecilomyces, Wallemia,* and *Curvularia Penicillium.*

Yeasts are eukaryotic microorganisms classified as members of the fungus kingdom with 1,500 species currently identified and are estimated to constitute 1% of all described fungal species. Yeasts are unicellular, although some species may also develop multicellular characteristics by forming strings of connected budding cells known as pseudohyphae or false hyphae. Most yeasts reproduce asexually by mitosis, and many do so by the asymmetric division process known as budding.

Yeasts do not form a single taxonomic or phylogenetic grouping. The term "yeast" is often taken as a synonym for *Saccharomyces cerevisiae*, but the phylogenetic diversity of yeasts is shown by their placement in two separate phyla: the Ascomycota and the Basidiomycota. The budding yeasts ("true yeasts") are classified in the order Saccharomycetales. The species are: *Arxula adeninivorans* (*Blastobotrys adeninivorans*)*, Candida boidinii, Schizosaccharomyces pombe, Saccharomyces cerevisiae, Saccharomyces carlsbergensis, Saccharomyces uvarum, Candida utilis, Candida albicans, Saccharomyces boulardii, Brettanomyces bruxellensis, Hansenula polymorpha* (*Pichia angusta*)*, Pichia pastoris, Kluyveromyces lactis, Yarrowia lipolytica,* and *Malassezia furfur.*

Pathogenic single-celled eukaryotes (may also be referred to as protozoans): *Entamoeba histolytica; Plasmodium; Giardia lamblia;* and *Trypanosoma brucei.*

Aspect 4F of the Fourth Aspect: Presence and/or Quantity of Cells Potentially Comprised in a Solution Human stem cells including neuronal stem cells, mammary stem cells, stems cells from skin, and hematopoietic stem cells are capable of growing in solution, wherein only a specific fraction of these stem cells is capable of forming colonies on a solid basis. This specific fraction is represented by the undifferentiated (progenitor) stem cells and it is of interest for several diagnostic and therapeutic applications to determine whether such undifferentiated stem cells are present in a cell solution comprising stem cells. Furthermore, the quantity of such cells in a solution is of interest for these applications and others. The method outlined in aspect 4F of the fourth aspect can thus also be referred to as clonogenic assay to determine the presence and/or quantity of undifferentiated stem cells. A clonogenic assay may also be referred to as "human colony forming cell (CFC) assay". A CFC is e.g. used in the study of hematopoietic stem cells. Hematopoietic progenitor cells are capable of proliferating and differentiating into colonies in a (semi)-solid medium in response to cytokine stimulation and the present method can thus further be referred to as a CFC assay to determine the presence and/or number of hematopoietic progenitor cells in a solution comprising hematopoietic stem cells.

Human cancer cells derived from well-known cancer cell lines or biopsies from patients suffering from cancer are also of particular relevance for aspect 4F of the fourth aspect because cancer cells can acquire stem cell-like properties (referred to as "cancer stem cell (CSC)-like" properties), including the ability to form colonies. Such cancer cells are referred to as CSCs. CSCs can e.g. be induced and generated in response to chemotherapeutic treatment. Accordingly, the efficacy of the chemotherapy decreases and it is of interest inter alia for the further therapy to find out whether such CSCs are present in a cancer cell population or not. To this aim, a clonogenic assay is carried out. Further information can e.g. be taken from Han et al., "*A2780 human ovarian cancer cells with acquired paclitaxel resistance display cancer stem cell properties*"; ONCOLOGY LETTERS 6: 1295-1298, 2014.

Therefore, the basic situation underlying aspect 4F is that a solution, preferably a cell suspension, comprising different types of preferably human stem or cancer cells is provided and that it is not known whether said solution comprises cells capable of forming colonies. The method of aspect 4F is capable of determining whether such cells are present in said solution. There may also be the situation that it has been generally determined that such cells are present in a solution, but the quantity of said cells in said solution is not known. The method of aspect 4F is capable of determining the quantity of such cells in said solution.

In an embodiment, aspect 4F thus relates to a method for determining the presence and/or quantity of cells potentially comprised in a solution, wherein said method comprises the steps of:
  a) Providing a solution potentially comprising cells;
  b) Providing a solid medium suitable for growth of said cells;
  c) Dispensing at least one defined volume of said solution provided in step a) onto said solid medium provided in step b) using acoustic liquid transfer;
  d) Incubating said solid medium under conditions suitable for growth of said cells and thus potentially obtaining colonies from said cells; and
  e) Determining the presence and/or number of said potentially obtained colonies, wherein
    1) the presence of colonies indicates that said cells are present in said solution; and
    2) the number of colonies correlates with the quantity of said cells in said solution such that the number of colonies indicates the quantity of said cells in said solution.

The method according to aspect 4F may also be referred to as "automated clonogenic method for determining the presence and/or quantity of cells potentially comprised in a solution" or "automated clonogenic assay for determining the presence and/or quantity of cells potentially comprised in a solution which comprises the afore-mentioned steps.

All of the above mentioned embodiments of the fourth aspect including aspects 4A, 4B, 4C and 4D also apply for aspect 4F.

It is clear from the above that the cells that can be analyzed in the present method are cells that are capable of forming colonies on a solid medium suitable for growth of the cells. Such cells are in particular undifferentiated (progenitor) stem cells and cancer stem cells. The undifferentiated stem cells are preferably human undifferentiated stem cells or mouse undifferentiated stem cells or undifferentiated monkey stem cells. Said undifferentiated stem cells may be neuronal stem cells, mammary stem cells, stem cells from the skin or hematopoietic stem cells. Said cancer stem cells can be leukemic stem cells but are also found in solid tumors, such as e.g. in cancers of the brain, breast, colon, ovary, pancreas and prostate, as well as in melanoma, multiple myeloma and non-melanoma skin cancer. Suitable solid media and growth conditions are known to the skilled person and can be found in standard text books.

In a fifth aspect, the present invention relates to the use of acoustic liquid transfer and an acoustic liquid transfer device, respectively, for determining the presence and/or quantity of microorganisms or cells potentially comprised in a solution. In a preferred embodiment at least one defined volume of a solution comprising microorganisms or cells is dispensed on a solid medium suitable for growth of said microorganisms or cells. Preferably, said acoustic liquid transfer device is an Echo Liquid Handler or an ATS Acoustic Liquid Dispenser.

In a preferred embodiment of the fifth aspect, the method according to the fourth aspect of the present invention is employed for determining the presence and/or quantity of microorganisms or cells potentially comprised in a solution.

In a sixth aspect, the present invention relates to the use of acoustic liquid transfer and an acoustic liquid transfer device, respectively, in a method according to the fourth aspect of the present invention. Preferably, said acoustic liquid transfer device is an Echo Liquid Handler or an ATS Acoustic Liquid Dispenser.

BRIEF DESCRIPTION OF THE DRAWINGS

The figures shown in the following are merely illustrative and shall describe the present invention in a further way. These figures shall not be construed to limit the present invention thereto.

FIG. 1A shows a spotting pattern used for spotted dilution plating, wherein spots of defined volumes were transferred to the solid medium along the indicated line in specific distances. The volume per individual spot along the indicated arrows ranged from a low volume (indicated as "X") to a high volume (indicated as "XX"), with linearly increasing volumes (indicated by arrows of different line width), as described in Example 1.

FIG. 1B shows bacterial colonies including discrete colonies and conglomerates of colonies in a culture plate comprising solid medium selective for positive transformants (by including ampicillin) after dispensing different volumes of three different bacterial transformation dilutions (A to C) onto the culture plate using acoustic liquid transfer and incubating same. In A, different volumes of a 1:100 dilution of the transformation reaction were dispensed; in B, different volumes of a 1:5 dilution of the transformation reaction were dispensed; and in C, different volumes of a 1:10 dilution of the transformation reaction were dispensed using a Labcyte Echo® acoustic liquid transfer device. The experiment was performed in duplicate and the distribution pattern on the plate and respective volumes are described in Example 1.

FIG. 2 Spiral spotting pattern suitable for rectangular multi-well plates

FIG. 3 depicts an automated way of obtaining discrete colonies of 24 different transformation reactions in parallel. The 24 different transformation reactions are exemplified by 6 reaction vials (C), wherein the volume lacking in the first three vials was already spotted onto the respective wells of a 24 well-plate. The spotting is carried out using an acoustic generator (A) for the production of focused sound waves (B), which eject a predetermined and specific volume from the solution in a vial to the well. The 24 well-plate (D), the "receiving plate", contains solid selective medium, in the present example LB agar supplemented with ampicillin. The spotting pattern for each well is depicted in FIG. 4A.

FIG. 4A shows the spotting pattern exemplified in example 3. The numbers of spots and the volumes of the transferred transformation solutions per spot are as follows: 1: 4 spots and 25 nl each spot; 2: 6 spots and 100 nl each spot; 3: 7 spots and 0.5 µl each spot; 4: 4 spots and 2 µl each spot; 5: 3 spots and 10 µl each spot.

FIG. 4B schematically depicts the colonies obtained after spotting and incubation, wherein discrete colonies can be identified (see arrows), automatically picked and then further screened.

FIG. 5A shows the spotting pattern exemplified in Example 4. 24 different solutions were transferred onto a tray plate containing one well. Each area (or "virtual well") comprises 64 spots of the same dilution and the same volume.

FIG. 5B shows the corresponding result. Single colonies were obtained for each of the 24 different transformations. Such colonies can be easily picked (e.g. colony picker) and further screened (e.g. PCR).

DEFINITIONS

Figure 1:
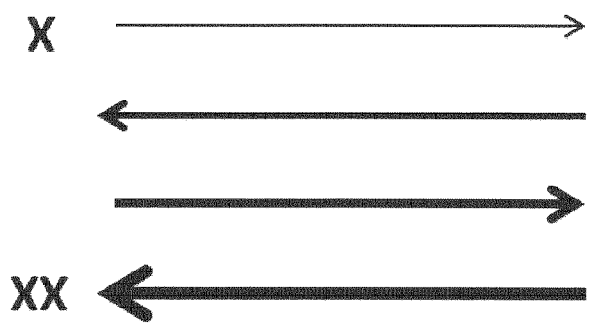
FIG. 1 Pattern of bacterial colonies in a selective culture plate
Figure 1:
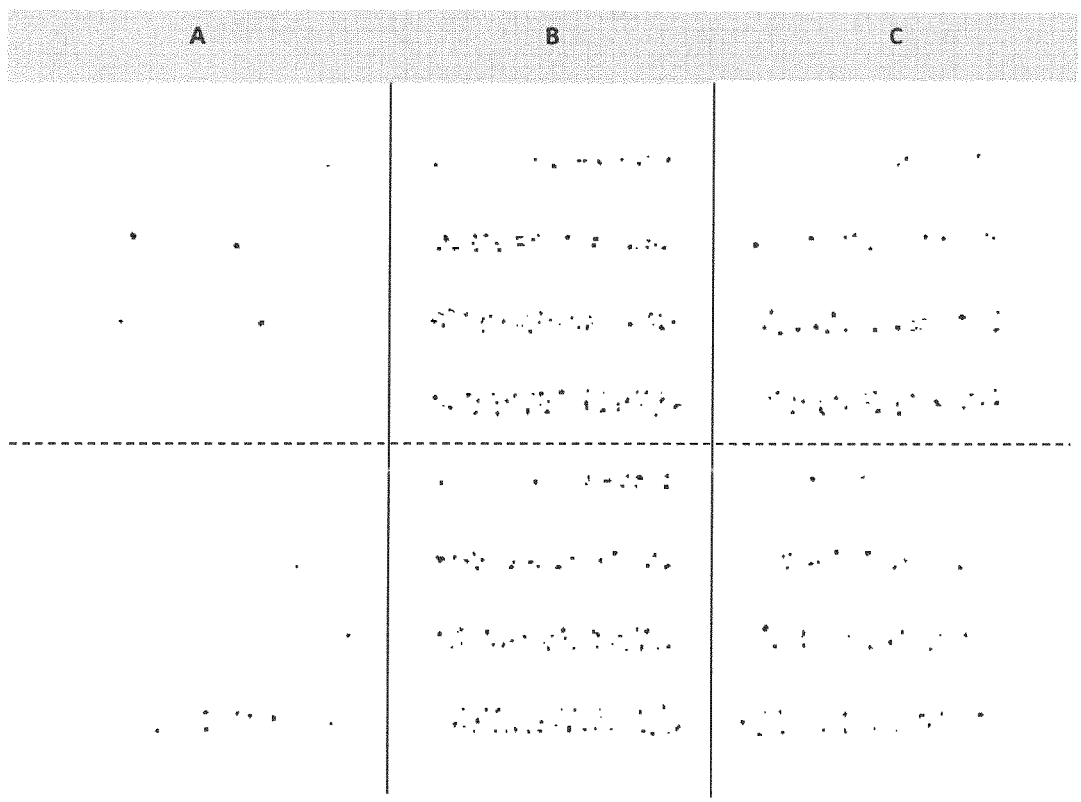

For the sake of clarity and readability the following definitions are provided. Any technical feature mentioned for these definitions may be read on each and every embodiment of the invention. Additional definitions and explanations may be specifically provided in the context of these embodiments.

As used in the specification and the claims, the singular forms of "a" and "an" also include the corresponding plurals unless the context clearly dictates otherwise.

The terms "about" and "approximately" in the context of the present invention denotes an interval of accuracy that a person skilled in the art will understand to still ensure the technical effect of the feature in question. The term typically indicates a deviation from the indicated numerical value of ±10% and preferably ±5%.

It needs to be understood that the term "comprising" is not limiting. For the purposes of the present invention, the term "consisting of" is considered to be a preferred embodiment of the term "comprising of". If hereinafter a group is defined to comprise at least a certain number of embodiments, this is also meant to encompass a group which preferably consists of these embodiments only.

The term "automated" as used herein refers to a situation where it is not necessary to carry out in particular the dispensing step c) by hands, i.e. manually, but wherein said solution and said medium are provided in steps a) and b) to (a) suitable device(s) (such as (a) robot(s) and/or an acoustic liquid transfer device), which is/are programmed prior to carrying out specific steps such that the corresponding steps and pattern(s), in particular the dispensing step c), are carried out in an automated fashion according to what has been programmed. It can also be automated (e.g. by using a robot) to provide said solid medium in a suitable distance from the acoustic liquid transfer device, to then remove said solid medium after step c) has been carried out, and to transfer said solid medium to a destination area for carrying out step d), the incubation. Likewise, it is preferably automated to provide said solution in step a) to an acoustic liquid transfer device, again using a robot or the like.

The term "discrete colony" as used herein means that a colony is present on a solid medium, which stems from a single colony-forming unit (CFU, that has formed the respective colony), and which is sufficiently far away from at least one further colony (i.e. there is a sufficient distance to said further colony) such that there is no (partial) overgrowth of these at least two colonies. Such a discrete colony has usually the shape of a hemisphere.

The term "microorganisms" as used herein refers to microorganisms capable of forming colonies on solid medium, in particular to bacteria, fungi (e.g. yeasts) and single-celled eukaryotes. Depending on the aspect of the invention, these microorganisms differ. Thus, in the first aspect as outlined above, it is preferred to use microorganisms which are routinely used in laboratories for carrying out standard procedures, such as e.g. cloning procedures, interaction analyses, recombinant expression of proteins, growth analyses and so on. In embodiments, where microorganisms comprise an exogenous nucleic acid, the plural form (i.e. "microorganisms") is used herein since a single microorganism is not used as "target" organism for introducing exogenous nucleic acid because the efficacy of introducing said exogenous DNA into a single microorganism would be too low. The plural as used in the method of the present invention does not mean that different strains of a microorganism are used and colonies from these different strains should be obtained in a single method not run in parallel. Rather, before this background, the plural means that several microorganisms of the same strain and/or the same clone are used. If, however, several different cloning experiments are carried out in parallel, and the aim of the present method is to in parallel provide discrete colonies from microorganisms comprising exogenous nucleic acid from different cloning experiments, the skilled person understands that different strains of microorganisms may indeed be used. In the fourth aspect of the invention, the focus is on the determination of the presence and/or quantity of microorganisms capable of forming colonies on a solid medium. In general, any of such microorganisms can be detected as long as the growth conditions are known. Of course, if the focus is on the detection in a biological sample, different strains of microorganisms and different microorganisms may be present in the liquid sample.

The term "cells" as used herein in particular refers to eukaryotic cells, preferably human cells, mouse cells, monkey cells or insect cells. Said eukaryotic cells may also be stem cells and in particular undifferentiated stem cells. Further, said eukaryotic cells may also be cancer cells. This is indicated in detail above and differs depending on the specific aspect of the invention.

The term "solution" as used herein is used interchangeably with the term "fluid" or the term "liquid" and means that something is provided in the liquid state, wherein at least one sample of said solution can be transferred to a given target by acoustic liquid transfer, preferably in the form of one or several defined volumes. The term "solution" thus includes all liquid states (such as e.g. states of different viscosities) that can generally be transferred to a given target by acoustic liquid transfer. A "suspensions" is usually included in this definition as well. The term "solution" as used herein does not mean that the respective solution may not contain or comprise certain elements, such as in particular microorganisms or cells. To the contrary, as is evident from the whole description of the present invention, said solution preferably comprises microorganisms or cells, depending on the aspect.

The term "solid medium" as used herein means a medium for microorganisms or cells, which does not allow for passive transfer of said microorganisms or cells within said medium but where a specific microorganism or cell transferred onto said solid medium will adhere to the spot of placement (if there is such an active mechanism) or simply stay on this spot once transferred there, e.g. in the form of a small volume of a liquid sample put onto a specific spot of said solid medium. The term "solid medium" further means that a liquid sample of a specific volume will adhere to the medium by the surface tension. The term "solid medium" thus includes all solid states (such as e.g. states of different viscosities) that are generally suitable for not allowing passive transfer within said medium and for holding a liquid sample at a specific spot. A particularly solid medium according to the present invention is agar, but semi-solid media and agars, respectively, are also encompassed, particularly for eukaryotic cells such as e.g. stem cells or cancer cells.

The term "culture plate" as used herein means a plate containing a solid medium (e.g., LB agar). These plates may contain one single well (e.g. Nunc™ OmniTray™) or multi wells. The term "culture plate containing a single well" as used herein means that the solid medium of the plate provides one plane area. Contrary thereto, multi well plates provide distinct areas of solid medium. Said distinct areas may be generated by walls.

The term "defined volume" as used herein is interchangeable with the term "specific volume".

The term "acoustic liquid transfer" is used herein interchangeably with the terms "acoustic ejection" and "acoustic droplet ejection", and is based on the principle to use a pulse of ultrasound to move a low volume of a fluid (such as e.g. pl, nl or µl) without any physical contact. This technology focuses acoustic energy into a fluid sample in order to eject droplets as small as a nanoliter or even a picoliter. "Acoustic liquid transfer" can be used to transfer samples without damage. To eject a droplet, a transducer generates and transfers acoustic energy to a source well. When the acoustic energy is focused near the surface of the liquid, a mound of liquid is formed and a droplet is ejected. The diameter of the droplet scales inversely with the frequency of the acoustic energy. Thus, higher frequencies produce smaller droplets. Unlike other liquid transfer devices, no pipette tips, pin tools, or nozzles touch the source liquid or destination surfaces. As mentioned above, the liquid is moved without any physical contact, thus the transducer does not directly contact the liquid to be ejected. Liquids ejected from the source are typically captured by the solid medium due to surface tension. For larger volumes, multiple droplets can be rapidly ejected from the source.

The term "exogenous" in combination with nucleic acid as used herein relates to nucleic acid that differs from nucleic acid naturally found and present ("endogenous") in the microorganisms or cells as used in the present method. In other words, this "exogenous" nucleic acid originates outside the respective microorganisms or cells. For the sake of clarity, it is noted that the expression "microorganisms or cells comprising an exogenous nucleic acid comprised in a solution" is interchangeable with the expression "microorganisms or cells comprised in a solution, wherein said microorganisms or cells comprise an exogenous nucleic acid". Thus, the exogenous nucleic acid is not meant as being comprised in a solution.

The term "DNA" as used herein is the usual abbreviation for deoxyribonucleic acid. It is a nucleic acid molecule, i.e. a polymer consisting of nucleotide monomers. These nucleotides are usually deoxy-adenosine-monophosphate, deoxy-thymidine-monophosphate, deoxy-guanosine-monophosphate and deoxy-cytidine-monophosphate monomers or analogs thereof which are—by themselves—composed of a sugar moiety (deoxyribose), a base moiety and a phosphate moiety, and polymerize by a characteristic backbone structure. The backbone structure is, typically, formed by phosphodiester bonds between the sugar moiety of the nucleotide, i.e. deoxyribose, of a first and a phosphate moiety of a second, adjacent monomer. The specific order of the monomers, i.e. the order of the bases linked to the sugar/phosphate-backbone, is called the DNA-sequence. DNA may be single-stranded or double-stranded. In the double stranded form, the nucleotides of the first strand typically hybridize with the nucleotides of the second strand, e.g. by A/T-base-pairing and G/C-base-pairing.

The term "RNA" as used herein is the usual abbreviation for ribonucleic acid. It is a nucleic acid molecule, i.e. a polymer consisting of nucleotide monomers. These nucleotides are usually adenosine-monophosphate, uridine-monophosphate, guanosine-monophosphate and cytidine-monophosphate monomers or analogs thereof, which are connected to each other along a so-called backbone. The backbone is formed by phosphodiester bonds between the sugar, i.e. ribose, of a first and a phosphate moiety of a second, adjacent monomer. The specific order of the monomers, i.e. the order of the bases linked to the sugar/phosphate-backbone, is called the RNA-sequence. Usually RNA may be obtainable by transcription of a DNA-sequence, e.g., inside a cell. In eukaryotic cells, transcription is typically performed inside the nucleus or the mitochondria. In vivo, transcription of DNA usually results in the so-called premature RNA which has to be processed into so-called messenger-RNA, usually abbreviated as mRNA. Processing of the premature RNA, e.g. in eukaryotic organisms, comprises a variety of different posttranscriptional-modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino acid sequence of a particular peptide or protein. Typically, a mature mRNA comprises a 5'-cap, optionally a 5'UTR, an open reading frame, optionally a 3'UTR and a poly(A) sequence. In addition to messenger RNA, several non-coding types of RNA exist which may be involved in regulation of transcription and/or translation, and immunostimulation.

The term "selective" as used herein means that, after incubation as defined herein, microorganisms or cells comprising exogenous nucleic acid can be distinguished from microorganisms or cells not comprising exogenous nucleic acid in a suitable way (e.g. by survival or colour). As described in detail above, a selection can also be based thereon that a specific insert is present or not in the exogenous nucleic acid comprised in the microorganisms or cells. In view of this, any reference to "microorganisms or cells comprising exogenous nucleic acid versus microorganisms or cells not comprising exogenous nucleic acid" is to be regarded as also referring to a situation of "microorganisms or cells comprising exogenous nucleic acid with an insert versus microorganisms or cells comprising exogenous nucleic acid without an insert". The distinguishing information in the latter case resides in the insert. In any case, the selectivity will be in favor of microorganisms comprising exogenous nucleic acid (or an insert therein), particularly if the selection is the viability (i.e. only microorganisms comprising exogenous nucleic acid or exogenous nucleic acid with an insert will survive and grow, and not the other way round in the meaning that only microorganisms not comprising exogenous nucleic acid or comprising exogenous nucleic acid without an insert will survive and grow).

The term "insert" as used herein refers to a specific exogenous nucleic acid sequence comprised in the exogenous nucleic acid. This sequence varies depending on the aim of the experiment, but the concept of selectivity based on the presence of an insert is in almost all cases that a specific functionality (e.g. the production of a specific functional part of an enzyme or the whole functional enzyme) is coupled to the insertion of the insert at the intended place at the exogenous nucleic acid. Thus, as outlined above for the β-galactosidase assay, the correct insertion of the insert results therein that no functional enzyme is present in the exogenous nucleic acid with insert comprised in the microorganisms, whereas a complemented, functional enzyme is present in microorganisms comprising the exogenous nucleic acid without an insert at the intended place.

The term "transformation"/"transforming" as used herein relates to a process, where exogenous nucleic acid is introduced into a microorganism. Typically, the receiving microorganisms are made competent for receiving the exogenous nucleic acid in order to increase the transfer rate. Usually, the process of making microorganisms artificially competent for receiving exogenous nucleic acid involves making the cell passively permeable to nucleic acid by exposing it to conditions that do not normally occur in nature. One way of achieving this is the incubation in a solution containing divalent cations (often calcium chloride) under cold conditions, before being exposed to a heat pulse (heat shock). Alternatively, electroporation is used. The way of making microorganism competent also depends on the type of microorganisms used. Thus, if e.g. E. coli strains are used, both of the afore-mentioned methods can be applied. For yeasts, such as e.g. S. cerevisiae, electroporation is typically used. Alternatively, yeast transformation may be based on the use of lithium acetate, polyethylene glycol, and single-stranded nucleic acid. Typical transformation protocols are known to the skilled person.

The term "transduction"/"transducing" as used herein is also a process, where exogenous nucleic acid is introduced into a microorganism or a eukaryotic cell. Transduction is the process by which nucleic acid is transferred into a microorganism or eukaryotic cell by a virus or via a viral vector. Usually, this involves the use of bacteriophages and is therefore sometimes also referred to as "infection"/"infecting". Typical transduction protocols are known to the skilled person.

The term "transfection" as used herein relates to a process, where exogenous nucleic acid is introduced into a eukaryotic cell. Transfection of eukaryotic cells typically involves opening transient pores or "holes" in the cell membrane to allow the uptake of exogenous nucleic acid. Transfection can be carried out using calcium phosphate, by electroporation, by cell squeezing or by mixing a cationic lipid with the material to produce liposomes, which fuse with the cell membrane and deposit their cargo inside. Typical transfection protocols are known to the skilled person.

The term "DNA plasmid" as used herein refers to a circular nucleic acid molecule, preferably to an artificial nucleic acid molecule. Such plasmid DNA constructs may be storage vectors, expression vectors, cloning vectors, transfer vectors etc. Preferably, a plasmid DNA within the meaning of the present invention comprises in addition to the elements described herein a multiple cloning site, optionally a selection marker, such as an antibiotic resistance factor, and a sequence suitable for multiplication of the vector, such as an origin of replication. Typical plasmid backbones are e.g. pUC18, pUC19 and pBR322.

The term "bacteriophage" is used herein in the meaning as commonly understood by the skilled person. Thus, reference is made to an organism that infects and replicates within a bacterium. A bacteriophage is composed of proteins that encapsulate a DNA or RNA genome, wherein the genome typically encodes as few as four genes, and as many as hundreds genes.

The term "cosmid" is used herein in the meaning as commonly understood by the skilled person. A "cosmid" is usually defined as a hybrid plasmid that contains a Lambda phage cos sequence (cos sites+plasmid=cosmid). Cosmids are often used as a cloning vector in genetic engineering. Cosmids can be used to build genomic libraries since they can contain rather large DNA sequences, such as 37 to 52 kb of DNA. Cosmids usually replicate as plasmids since they have a suitable origin of replication and frequently also contain a gene for selection. Unlike plasmids, cosmids can also be packaged in phage capsids, which allows the foreign genes to be transferred into or between cells by transduction.

The term "artificial chromosome" as used herein is a DNA construct, which contains genes that promote the even distribution of plasmids after cell division. Usually, reference is made to "BACs", "bacterial artificial chromosomes, and "YACs", "yeast artificial chromosomes". BACs usually have an insert with a size of 150 to 350 kbp and may e.g. be used for sequencing the genome of organisms in genome projects. A short piece of the organism's DNA is amplified as an insert in BACs, and then sequenced. YACs are genetically engineered chromosomes derived from the DNA of the yeast, which is then ligated into a bacterial plasmid. By inserting large fragments of DNA, from 100 to 1000 kb, the inserted sequences can be cloned and physically mapped using a process called chromosome walking. YACs usually contain an autonomously replicating sequence (ARS), centromere and telomeres and a selection marker.

A "determination of the presence of microorganisms or cells comprised in a solution" is particularly relevant for diagnostic purposes, namely to find out whether specific microorganisms or cells are present in a solution. Such a solution is preferably a sample as indicated above, if the presence and/or quantity of microorganisms should be determined. If the sample is e.g. food, it may be determined whether specific microorganisms (such as e.g. pathogens) are present in said sample. This also applies to a situation where the solution is e.g. blood, and the purpose is to determine whether microorganisms of a specific pathogen are present in the blood. As outlined above, as regards the determination of the presence and/or quantity of cells, this mainly relates to specific stem cell populations and cancer stem cells (CSCs).

A "determination of the quantity of microorganisms or cells comprised in a solution" is particularly relevant if it known from other analyses that specific microorganisms or cells are present in a solution, but it is not known, in which quantity said microorganisms or cells are present. Thus, e.g. for specific microorganisms in food or for specific CSCs of a cancer type, there may be a threshold concentration for said microorganisms or cells. This may have an impact on the consumption of the food or the further cancer therapy. Using, the present method of determining the quantity of microorganisms or cells comprised in a solution, it is possible to provide an answer whether the microorganisms or cells are present below or above said threshold concentration, in particular if the colony-numbers of reference samples are known. In general, the number of colonies correlates with the quantity of said microorganisms or cells in said solution such that a high number of colonies indicates a high quantity of said microorganisms or cells in said solution. Accordingly, a low number of colonies indicates a low quantity of said microorganisms or cells in said solution.

It is preferred for the afore-mentioned determination method and in particular the method for determining the quantity of microorganisms or cells comprised in a solution to carry out the method as described herein and to then compare the results, i.e. the number of colonies obtained by the method, to a reference with a known number of microorganisms or cells in a specific volume (i.e. a specific known concentration of said microorganisms or cells in a solution). Of course, the parameters of the method as described herein and the reference method must be substantially identical. This inter alia relates to i) the type of solution; ii) the dilution (if any) of said solution; iii) the medium provided in step b); and iv) the defined volume dispensed in step c).

Detailed Description of the Findings Underlying the Present Invention

Transformation efficiency usually varies between different transformation reactions, different transformation techniques and different plasmid constructs. This is problematic as it usually requires additional procedural steps to obtain discrete bacterial colonies. For example, if the transformation efficiency was high, it is possible that plating of bacteria (in a certain dilution) on agar plates leads to an overgrowing of bacteria, which makes it impossible to isolate discrete colonies. On the other hand, if the transformation efficiency was low, it is possible that hardly any discrete colony is growing. Both cases are problematic for down-stream analyses.

The present invention is inter alia based on the finding that an acoustic liquid handling device can be used for generating discrete colonies, wherein the device employs acoustic ejection to transfer individual "drops" of a liquid transformation culture (with unknown concentration of bacteria carrying a plasmid) in a customized pattern onto culture plates (e.g., plates containing a single well or multi well plates) containing solid growth medium (e.g., LB agar).

By spotting different volumes of liquid onto different areas of the culture plates, a gradient of bacterial culture can e.g. be generated (which may be referred to as "spotted dilution plating") that allows the isolation of discrete colonies from several different transformation cultures in a single procedural step.

This procedure may be applied on one culture plate containing a single well (e.g. Nunc™ OmniTray™) in a parallel manner, wherein the different gradients for each transformation reactions are spotted on defined areas on the culture plate (e.g., different volumes per spot of 24 different transformation reactions are spotted on 24 different areas on the plate). It has to be noted that such a setup (spotting of 24 different transformations on 24 distinct areas on a single-well plate such as Nunc™ OmniTray™) improves the automated picking of single discrete colonies. Particularly, as no well walls were present, detection and picking of colonies is strongly improved. Of course, the inventive method as outlined herein also allows for the spotting of 48, 96 or even more different transformations onto a single-well plate such as Nunc™ OmniTray™ which would further economize the high throughput cloning and screening.

Alternatively, the procedure may be applied in a multi-well plate format where each transformation reaction is spotted on each well (e.g., different volumes per spot of 24 different transformation reactions are spotted on 24 different wells).

The present method allows for a streamlined, robust, cost-effective and ecologic way of obtaining discrete colonies from one or several transformation reactions in parallel. The discrete colonies can then be isolated and used for further downstream screening analyses.

However, also spotting of equally defined volumes allows the isolation of discrete colonies from different transformation cultures in a single procedural step. If e.g. 6.08 µl transformation reaction are used for spotting of 64 equally defined volumes (i.e. an equally defined volume of 95 nl per spot), discrete colonies may be isolated for transformation reactions that comprise a different concentration of colony-forming units (CFUs). For instance, a transformation reaction may comprise 4 CFUs per 6.08 µl transformation reaction or 40 CFUs per 6.08 µl transformation reaction. Although the CFU concentrations differs in such a case by a factor of ten, four discrete colonies may be isolated for both transformation reactions if 64 spots of 95 nl are spotted onto the culture plate.

This procedure may be applied on one culture plate containing a single well (e.g. Nunc™ OmniTray™) in a parallel manner, wherein the different transformation reactions are spotted on defined areas on the culture plate (e.g., different volumes per spot of 24 different transformation reactions are spotted on 24 different areas on the plate). It has to be noted that such a setup (spotting of 24 different transformations on 24 distinct areas on a single-well plate such as Nunc™ OmniTray™) improves the automated picking of single discrete colonies. Particularly, as no well walls were present, detection and picking of colonies is strongly improved. Of course, the inventive method as outlined herein also allows for the spotting of 48, 96 or even more different transformations onto a single-well plate such as Nunc™ OmniTray™ which would further economize the high throughput cloning and screening.

The present method allows for a streamlined, robust, cost-effective and ecologic way of obtaining discrete colonies from one or several transformation reactions in parallel. The discrete colonies can then be isolated and used for further downstream screening analyses.

The inventors further realized that the underlying principle for the above method may also be employed i) in an automated method for obtaining at least one discrete colony from cells, in particular eukaryotic cells (e.g. from transfected eukaryotic cells in gene therapy) and ii) for determining the presence and/or quantity of microorganisms or cells potentially comprised in a solution. Also for this method, a high-throughput analysis of samples in parallel is possible, which provides further for the above-mentioned advantages of cost-effectiveness and a reduced risk of contamination.

PREFERRED EMBODIMENTS OF THE PRESENT INVENTION

In the following, further preferred embodiments of the present invention are described.

1. An automated method for obtaining at least one discrete colony from microorganisms comprising exogenous DNA comprised in a solution, the method comprising the steps of:
   a) Providing a solution comprising microorganisms comprising exogenous DNA;
   b) Providing a solid medium selective for microorganisms comprising exogenous DNA;
   c) Dispensing at least one defined volume of said solution provided in step a) onto said solid medium provided in step b) using acoustic liquid transfer; and
   d) Incubating said solid medium under conditions suitable for growth of microorganisms comprising exogenous DNA and thus obtaining at least one discrete colony.
2. The method according to claim 1, wherein the solution comprises an undefined number of colony-forming units.
3. The method according to embodiment 1 or 2, wherein said microorganisms comprising exogenous DNA are obtained by transforming or transducing microorganisms with said exogenous DNA prior to step a).
4. The method according to any one of the preceding embodiments, wherein said exogenous DNA is a DNA plasmid.
5. The method according to any one of the preceding embodiments, wherein said exogenous DNA encodes for a selection marker and wherein said solid medium selective for microorganisms comprising exogenous DNA is selective for expression of said selection marker in microorganisms comprising exogenous DNA.
6. The method according to any one of the preceding embodiments, wherein said acoustic liquid transfer is carried out by an acoustic liquid transfer device, preferably an Echo Liquid Handler or an ATS Acoustic Liquid Dispenser.
7. The method according to any one of the preceding embodiments, wherein said method is carried out in parallel with at least two solutions comprising microorganisms comprising exogenous DNA.
8. The method according to any one of the preceding embodiments, wherein the microorganisms are selected from the group consisting of *Escherichia coli*, *Corynebacterium*, *Pseudomonas fluorescens*, *Streptomyces*, *Arxula adeninivorans*, *Yarrowia lipolytica*, *Candida boidinii*, *Saccharomyces cerevisiae*, *Schizosaccharomyces pombe*, *Hansenula polymorpha*, *Pichia pastoris*, *Aspergillus*, *Trichoderma* and *Myceliophthora thermophile*.
9. The method according to any one of the preceding embodiments, wherein said at least one defined volume is selected from a range of from 1.0 nl to 100 µl.
10. The method according to any one of embodiments 1 to 9, wherein at least two equally defined volumes are dispensed in step c).
11. The method according to embodiment 10, wherein said at least two equally defined volumes are selected from a range of from 2.5 nl to 500 µl.
12. The method according to embodiment 10 or 11, wherein in total a volume from a range of from 100 nl to 50 µl is dispensed onto said solid medium.
13. The method according to any one of embodiments 1 to 9, wherein at least two differently defined volumes are dispensed in step c).
14. The method according to embodiment 13, wherein said at least two differently defined volumes are selected from a range of from 1.0 nl to 100 µl, wherein each volume is preferably selected close to an end of this range and opposite from the other volume.
15. The method according to embodiment 14, wherein said range of volumes is from 2.5 nl to 1 µl.
16. The method according to any one of embodiments 10 to 16, wherein said defined volumes are dispensed in a defined distance from each other.
17. The method according to embodiment 16, wherein said defined distance is at least 100 µm.
18. The method according to any one of the preceding claims, wherein said method is carried out in parallel with at least two solutions comprising microorganisms or cells.
19. The method according to any of the preceding claims, wherein said method is carried out on a culture plate containing a single well.
20. The method according to any one of embodiments 1 to 9, comprising the steps of:
    a) Providing a solution comprising microorganisms comprising exogenous DNA;
        1) Diluting said solution provided in step a); and
        2) Providing at least two differently diluted solutions;
    b) Providing a solid medium selective for microorganisms comprising exogenous DNA;
    c) Dispensing a defined volume of each of said at least two differently diluted solutions provided in step a)2) onto said solid medium provided in step b) using acoustic liquid transfer; and
    d) Incubating said solid medium under conditions suitable for growth of microorganisms comprising exogenous DNA and thus obtaining at least one discrete colony.
21. The method according to embodiment 20, wherein said defined volume is selected from a range of volumes from 1.0 nl to 100 µl.
22. The method according to embodiment 20 or 21, wherein said defined volumes are dispensed in a defined distance from each other.
23. The method according to embodiment 22, wherein said defined distance is at least 100 µm.
24. The method according to any one of embodiments 20 to 23, wherein said method is carried out in parallel with at least two solutions comprising microorganisms or cells.
25. The method according to any one of embodiments 20 to 24, wherein said method is carried out on a culture plate containing a single well.
26. Use of an acoustic liquid transfer device for obtaining at least one discrete colony from microorganisms comprising exogenous DNA.

EXAMPLES

The following Examples are merely illustrative and shall describe the present invention in a further way. These Examples shall not be construed to limit the present invention thereto.

Example 1: Spotted Dilution Plating of Three Different Bacterial Transformation Dilutions on Specific Areas of a Culture Plate Using Acoustic Liquid Transfer The aim of this example was to find out whether discrete colonies can be obtained in an automated manner suitable for a high-throughput method using acoustic liquid transfer when starting from differently diluted transformation solutions.

50 µl of competent $E.\ coli$ DH10B (MAX efficiency, Invitrogen) were transformed with 50 pg of a pUC19 DNA (provided with the competent cells by Invitrogen). Transformation procedures were carried out according to the manufacturer's instructions. After incubation at 37° C. in S.O.C. medium for 1 h, dilutions of the incubated transformation solution comprising $E.\ coli$ cells were performed in S.O.C. medium, namely A: 1:100; B: 1:5; and C: 1:10. Thus, solutions A and B differ by a dilution factor of 50, which is quite substantial when starting from the above-mentioned transformation solution.

Samples of solutions A, B and C were transferred to a destination culture plate using acoustic liquid transfer. The destination plate was a Nunc™ OmniTray™ (Thermo Fisher) filled with solid LB Agar supplemented with 100 µg/ml ampicillin. The ampicillin is used to select for the desired transformants carrying the pUC19 DNA, which are resistant to ampicillin due to the ampicillin-marker present and expressed on the pUC19 DNA. Thus, each colony growing on the solid LB Agar supplemented with ampicillin is derived from a positive transformant (so called colony-forming unit [CFU]), wherein discrete colonies will be subject to further analysis.

Acoustic liquid transfer was performed with a Labcyte Echo® 555 acoustic liquid transfer device onto the destination culture plate. The distribution pattern described in the following was generated using the Echo® Array Maker software. The culture plate was distributed into three areas, "A" for receiving fluids from solution A, "B" for receiving fluids from solution B, and "C" for receiving fluids from solution C, see FIG. 1, solid lines separating the three areas. Since the experiment was performed in duplicate, see FIG. 1, dashed line, there were overall six areas on the destination culture plate. In each area, the volumes per spot started from 5 nl/spot (2 volume units of 2.5 nl) linearly increasing to 197.5 nl/spot (75 volume units of 2.5 nl) with a spot-to-spot distance of 800 µm, and a total number of 520 spots. The distribution pattern was generated using the Echo® Array Maker software and the spotting pattern is shown in FIG. 1A.

After spotting by acoustic liquid transfer, the culture plate was incubated at 37° C. for 16 h to allow for growth and a picture of the plate was taken. This picture is shown in FIG. 1B.

As can be taken from FIG. 1B, it was possible for all three solutions A, B and C to obtain discrete colonies. Thus, discrete colonies derived from solution A (highest dilution) can be predominantly found in the spots that received higher volumes, whereas discrete colonies derived from solution B (lowest dilution) can already be found in the spots that received only 5 nl of the corresponding transformation solution. It is noted that, using the higher volumes of solution B, more conglomerates of colonies were obtained, see FIG. 1B, region B and spotting line with the higher volumes closer to "XX". Accordingly, due to the formation of conglomerates in these regions, the discrete colonies in other regions, namely from the lower volumes of solution B, would be subject to further analysis.

It is noted that the setup of the present experiment mimics situations, where i) the number/concentration of competent cells used in the transformation reactions varies to a significant degree between at least two reactions and ii) the transformation efficacy varies to a significant degree between at least two reactions (e.g. because of the use of different plasmids). Solution A as the highest dilution thus mimics a situation, where a rather low number of competent cells is used or where only a rather low number of transformed competent cells can be found in the resulting transformation solution, whereas solution B mimics a situation, where a high number of competent cells is used or where a high number of transformed competent cells can be found in the resulting transformation solution. As discussed above, discrete colonies can be obtained for each dilution and thus for each situation.

Overall, example 1 shows that the method applied therein is suitable for obtaining discrete colonies when starting from bacterial transformation solutions that are highly different in competent bacterial cell number/concentration or in transformation efficiency.

Example 2: Spotted Dilution Plating of a Bacterial Transformation Solution in Different Spot-to-Spot Distances and Different Volumes on a Multi-Well Culture Plate Using Acoustic Liquid Transfer The aim of this example was to find out whether the spotted dilution plating generates discrete colonies in a robust way by varying the spotting parameters (different volumes, different spot-to-spot distances). Additionally, a space-saving spotting pattern that is advantageous for automated colony picking was tested.

Figure 2A:
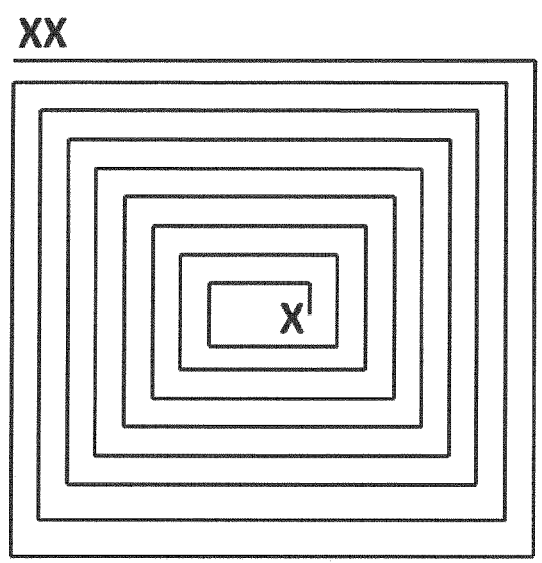
FIG. 2A shows a spiral spotting pattern that is suitable for a rectangular well, wherein spots of defined volumes are transferred to the well along the indicated line in specific distances. The volume per individual spot along the indicated line ranged from a high volume (indicated as "XX") to a low volume (indicated as "X"), see also Table 1 and Example 2.

The transformation procedure was performed as described in example 2. For the transfer on a multi-well plate with 12 individual rectangular wells, solution C (1:10) was used. Liquid transfer was performed with a Labcyte Echo® 555 acoustic liquid transfer device. Solution C was transferred to each of the 12 different wells in a spiral spotting pattern (see FIG. 2A), starting with the highest volume per spot at the margin of the well (indicated with "XX" in FIG. 2A and Table 1) and ending with the lowest volume in the center of the well (indicated with "X" in FIG. 2A and Table 1). For each well, different spiral spotting patterns were generated, using different volumes and spot-to-spot distances as indicated in Table 1.

TABLE 1

Distribution pattern of the generated spotted serial dilutions

| Setup | Total volume | number of spots | spot-to-spot distance | Volume of spot X | Volume of spot XX |
|---|---|---|---|---|---|
| A1 | 3 µl | 400 | 800 µm | 2.5 nl | 15 nl |
| B1 | 3 µl | 100 | 1600 µm | 2.5 nl | 60 nl |
| C1 | 3 µl | 49 | 2500 µm | 2.5 nl | 122.5 nl |
| A2 | 5 µl | 400 | 800 µm | 2.5 nl | 25 nl |
| B2 | 5 µl | 100 | 1600 µm | 2.5 nl | 100 nl |
| C2 | 5 µl | 49 | 2500 µm | 2.5 nl | 205 nl |
| A3 | 7 µl | 400 | 800 µm | 2.5 nl | 35 nl |
| B3 | 7 µl | 100 | 1600 µm | 2.5 nl | 140 nl |
| C3 | 7 µl | 49 | 2500 µm | 2.5 nl | 285 nl |
| A4 | 14 µl | 400 | 800 µm | 2.5 nl | 70 nl |
| B4 | 14 µl | 100 | 1600 µm | 2.5 nl | 280 nl |
| C4 | 14 µl | 49 | 2500 µm | 2.5 nl | 572.5 nl |

After spotting by acoustic transfer, the culture plate was incubated at 37° C. for 16 h and a picture of the plate was taken. This picture is shown in FIG. 2B.

Figure 2B:
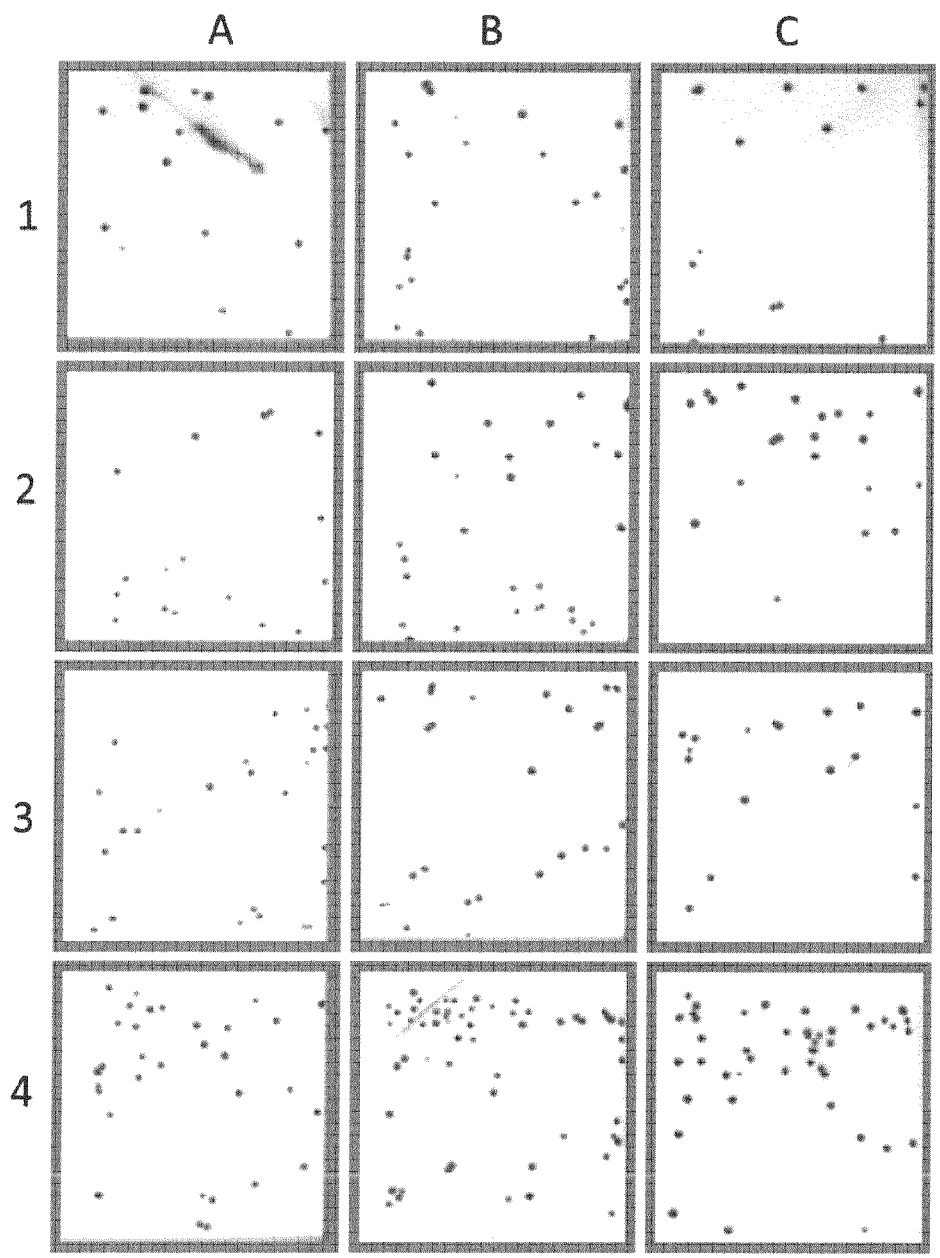
FIG. 2B shows a picture of a plate with 12 rectangular wells after incubation, where the spotting pattern of FIG. 2A for each well and as described in Example 2 was used. Discrete colonies and conglomerates of colonies can be identified.

As can be derived from FIG. 2B, the spotted dilution plating using acoustic liquid transfer is a robust method that generates single discrete colonies over a broad range of spotting parameters (volumes, number of spots, spot-to-spot distance). It is noted that using a setup with a larger number of spots (Table 1, setup A1-A4; see FIG. 2B), the distribution of colonies was most homogeneous. Moreover, using the spiral spotting pattern (FIG. 2A), more single discrete colonies were generated in the central area of a well (see for example well 4A or 4B), which is an advantageous attribute for automated colony picking devices. Thus, after incubating the plate, discrete colonies can be identified using commercially available image assisted colony detection software (based on diverse visual criteria such as shape, discreteness, and color) and discrete colonies can be picked automatically using commercially available colony picker and can be used for further analysis. For automated colony picking it is advantageous when single discrete colonies are localized in the center of a well, which can be achieved given the spotting pattern shown in FIG. 2A.

Therefore, such a method is robust and broadly applicable for high-throughput spotted dilution plating of transformation solutions with an unknown number of positive transformants (i.e. an unknown CFU content).

Figure 3:
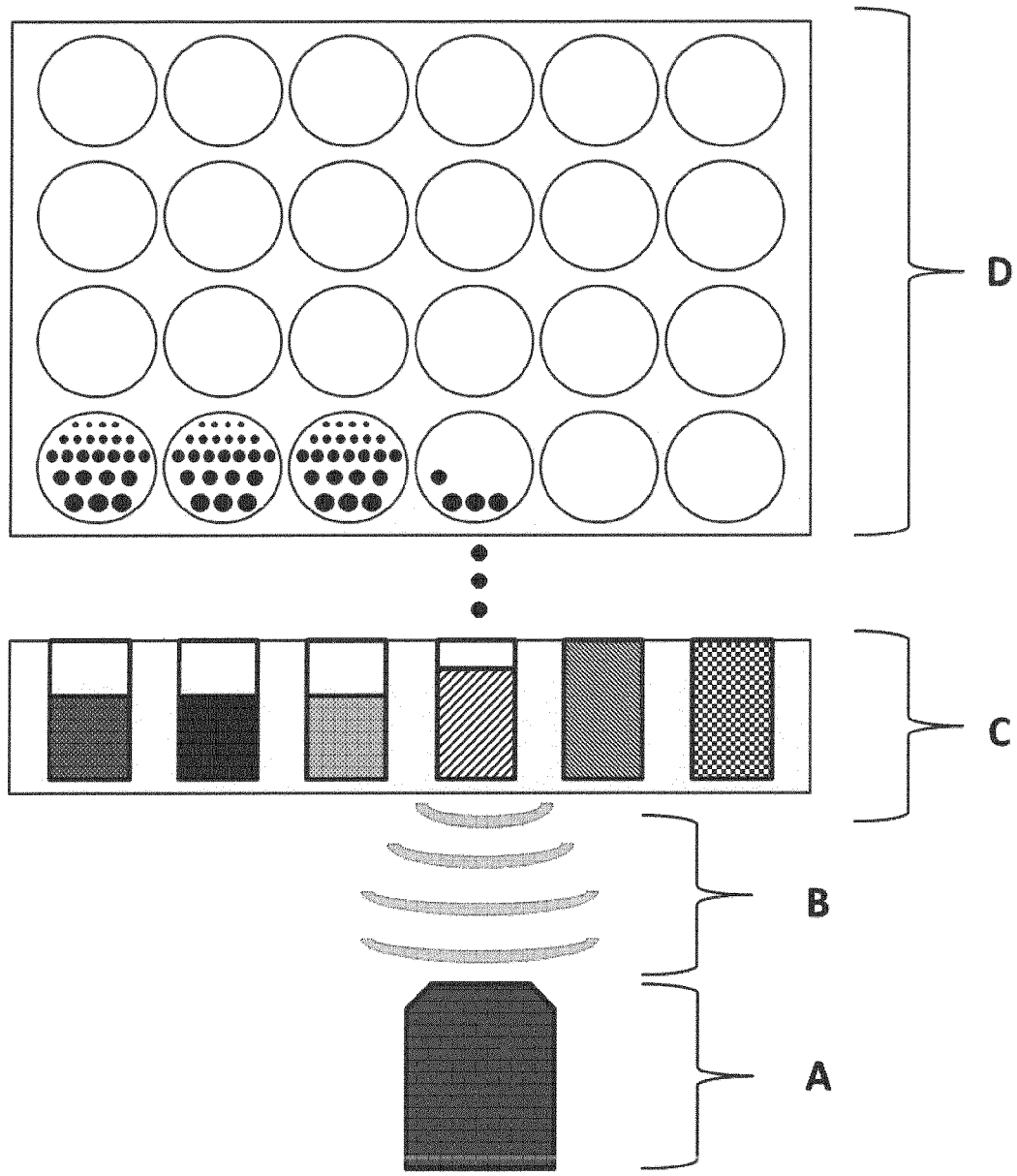
FIG. 3 Scheme of the spotting of different volumes of 24 different transformation reactions using acoustic liquid transfer in order to obtain discrete colonies

Example 3: Automated Spotted Dilution Plating of Bacterial Transformations in a 24 Well Plate Using Acoustic Liquid Transfer 24 transformation reactions using different plasmids (these plasmids differ by their respective inserts) are carried out. For each reaction, 50 µl of competent E. coli DH10B (MAX efficiency, Invitrogen) are transformed with 50 pg of pUC19 DNA (provided with the competent cells by Invitrogen) carrying a respective DNA insert (thus, in total, 24 different pUC19 constructs are used). Transformation procedures are carried out according to the manufacturer's instructions. After incubation of the transformation solutions at 37° C. in S.O.C. medium (provided with the competent cells by Invitrogen) for 1 h, each transformation solution is diluted 1:20 in S.O.C. medium. The resulting 24 dilutions are transferred to a destination plate using acoustic transfer (as shown in FIG. 3). A destination plate is a 24 well culture plate filled with solid LB Agar supplemented with 100 µg/ml ampicillin. This transfer step can be carried out fully automatically and in a high-throughput manner as described in the following.

Liquid transfer is performed with a Labcyte Echo® 555 acoustic liquid transfer device or an ATS Acoustic Liquid Dispenser (EDC Biosystems). In total, 42.2 µl of each afore-mentioned dilution is transferred to an individual well of the destination plate by acoustic transfer using several distinct smaller volumes as outlined in Table 2 and FIGS. 3 and 4. For each well, the volume is transferred in separate volume units of 2.5 nl to form spotted lines in the well with variable volumes spotted onto each spot, with a distance of 800 µm between each spot. The distribution pattern is generated using the appropriate software, such as the Echo® Array Maker software.

TABLE 2

Figure 4:
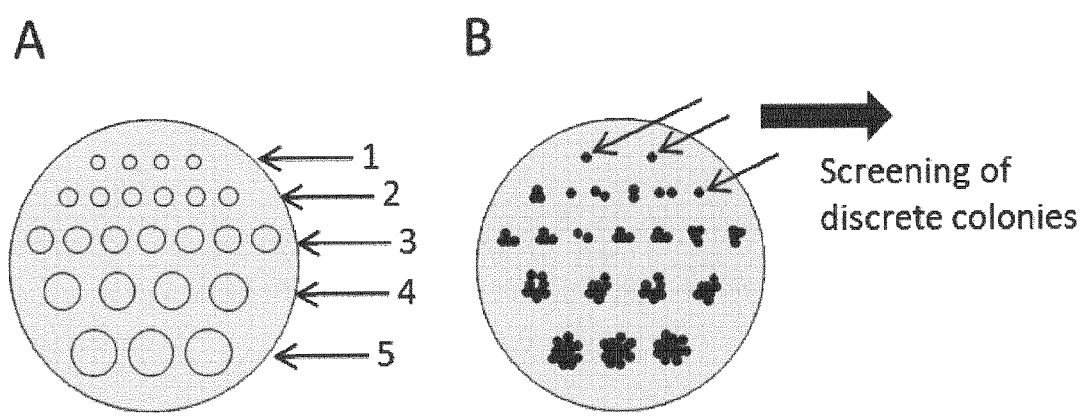
FIG. 4 Spotting pattern suitable for a round well of a multi-well plate

Distribution pattern of the generated spotted serial dilution (see also FIG. 4)

| Line | spots | Individual volume units of 2.5 nl per spot | Total volume per spot |
|---|---|---|---|
| 1 | 4 | 10 | 25 nl |
| 2 | 6 | 40 | 100 nl |
| 3 | 7 | 200 | 500 nl |
| 4 | 4 | 800 | 2000 nl |
| 5 | 3 | 4000 | 10000 nl |

The 24 different transformation dilutions are spotted onto the 24 wells of the destination plate, see FIG. 3. The plate is then incubated at 37° C. for 16 h to allow for growth of positive transformants.

Following the incubation period, discrete colonies per well can automatically be identified using cameras and commercially available image-assisted colony detection software (such as e.g. easyPick by Hamilton). Discrete colonies are then automatically picked using a commercially available colony picker (such as e.g. easyPick in combination with STAR by Hamilton or Evo colony picking by Tecan) and may be subject to further analysis, such as DNA sequencing of the inserts.

Example 4: Automated Spotted Plating of Bacterial Transformations in a Tray Plate Using Acoustic Liquid Transfer The aim of this example was to find out whether spotting of equally defined volumes may be used for generating discrete colonies in a robust way for different transformation reactions.

For preparing the transformation reactions, 1 µl of competent *E. coli* DH10B (MAX efficiency, Invitrogen), 0.5 µl ligation reaction, and 11 µl SOC medium were used. Ligation and transformation conditions were selected in such a way that 12.5 µl transformation reaction of a 3221 bp vector ligated to an 1636 bp insert comprise approximately 40 colony-forming units [CFUs].

24 transformation reactions comprising different DNA inserts (having different insert sizes) were carried out. The resulting 24 reactions were transferred to a destination plate using acoustic transfer. The destination plate was an Omni™ Tray™ plate (single well plate) filled with solid LB Agar supplemented with 100 µg/ml kanamycin. This transfer step was carried out fully automatically and in a high-throughput manner as described in the following.

Liquid transfer was performed with a Labcyte Echo® 550 acoustic liquid transfer device. In total, 6.08 µl of each afore-mentioned transformation reaction was transferred to an individual rectangular area of the destination plate by acoustic transfer (see FIG. 5A). For each area, 64 individual spots were spotted per area (95 nl per spot), with a center to center distance of 1700 µm between each spot. The distribution pattern (24 areas) was generated using the appropriate software, such as the Echo® Array Maker software.

Figure 5:
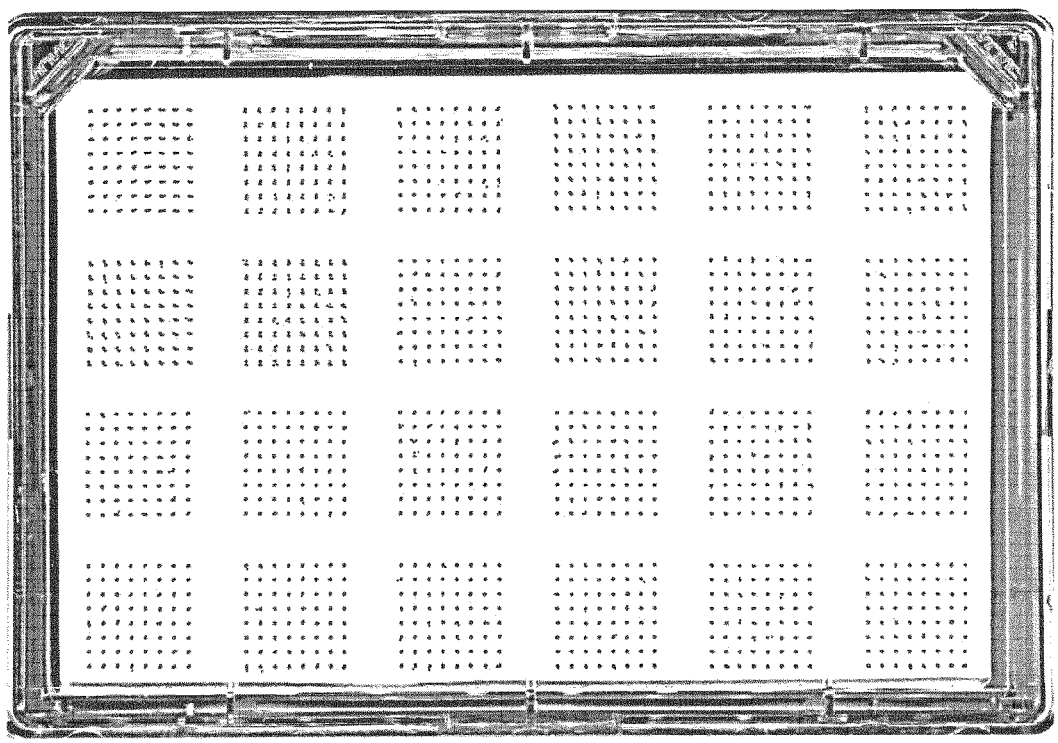
FIG. 5 Spotting pattern suitable for tray plate
Figure 5:
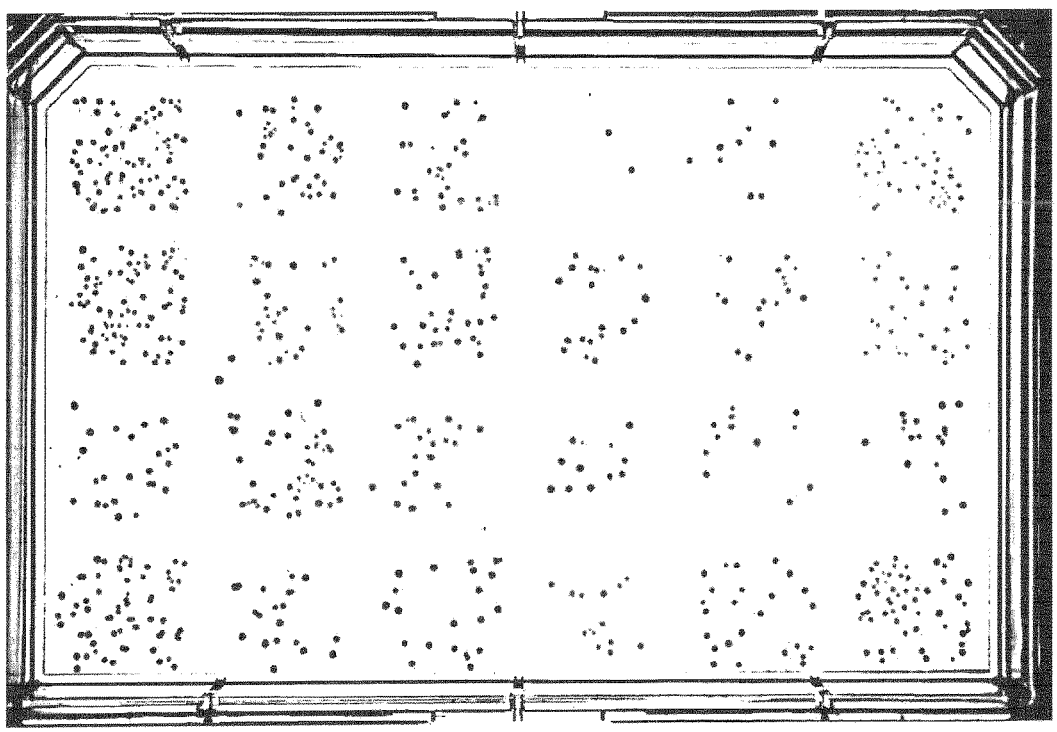

The 24 different transformations were spotted in parallel onto the tray plate of the destination plate (see FIG. 5A). Thus, 95 nl droplets of the 24 transformation reactions were spotted in parallel on 24 different areas of the plate. Following that, the plate was incubated at 37° C. for 16 h to allow for growth of colonies.

Following the incubation period single discrete colonies grew in each individual area (see FIG. 5B). Discrete colonies per area were automatically identified using cameras and commercially available image-assisted colony detection software (such as e.g. easyPick by Hamilton). 3-5 discrete positive colonies (identified with blue-white selection) were then automatically picked using a commercially available colony picker (such as e.g. with STAR by Hamilton) and subjected to further analysis, such as colony PCR and DNA sequencing of the inserts.

As can be derived from FIG. 5B, the spotted plating using acoustic liquid transfer is a robust method that generates single discrete colonies in a HT-compatible and robot-compatible manner.

Overall, example 4 shows that the method applied therein is suitable for obtaining discrete colonies when starting from bacterial transformation solutions that are different regarding the number of colony-forming units (CFUs). It is noted that the method allows the isolation of discrete colonies for short DNA inserts (e.g. 595 bp) as well as long DNA inserts (e.g. 4285 bp).

Therefore, such a method is robust and broadly applicable for high-throughput spotted plating of transformation solutions with an unknown number of positive transformants (i.e. an unknown CFU content).

The invention claimed is:

1. An automated method for obtaining at least one discrete colony from microorganisms or cells comprised in a solution, the method comprising the steps of:
    a) transforming or transducing microorganisms or cells with an exogenous nucleic acid comprising selection marker and providing a solution comprising the microorganisms or cells;
    b) providing a solid medium suitable for growth of said microorganisms or cells selective for said microorganisms or cells comprising the exogenous nucleic acid;
    c) dispensing at least two differently defined volumes of said solution provided in step a) onto said solid medium provided in step b) using acoustic liquid transfer, said at least two differently defined volumes being selected from a range of from 1.0 nl to 100 µl, wherein said acoustic liquid transfer comprises using a transducer which generates and transfers acoustic energy, and wherein said transducer does not directly contact said solution, wherein the at least two differently defined volumes are dispensed at a distance of at least 100 µm apart; and
    d) incubating said solid medium under conditions suitable for growth of said microorganisms or cells and thus obtaining at least one discrete colony of living microorganisms or cells comprising the exogenous nucleic acid.

2. The method according to claim 1, wherein said solution comprises an undefined number of colony-forming units.

3. The method according to claim 1, wherein in total a volume of said solution comprising microorganisms or cells from a range of from 100 nl to 50 µl is dispensed onto said solid medium.

4. The method according to claim 1, wherein said at least two differently defined volumes are selected from a lower end and an upper end of said range close to an end of the volume range and opposite from the other volume.

5. The method according to claim 1, wherein said method is carried out in parallel with at least two solutions comprising microorganisms or cells.

6. The method according to claim 1, wherein said method is carried out on a culture plate containing a single well.

7. The method of claim 1, wherein the solution comprises an unknown number of microorganisms or cells.

8. The method of claim 1, wherein the microorganisms or cells are bacterial cells.

9. The method of claim 8, wherein the bacterial cells are *E. coli*.

10. The method of claim 8, wherein the selection marker provides resistance to an antibiotic.

11. The method of claim 10, wherein the antibiotic is ampicillin and/or kanamycin.

* * * * *

UNITED STATES PATENT AND TRADEMARK OFFICE
CERTIFICATE OF CORRECTION

PATENT NO. : 11,225,682 B2
APPLICATION NO. : 15/767481
DATED : January 18, 2022
INVENTOR(S) : Isabel Reichert et al.

It is certified that error appears in the above-identified patent and that said Letters Patent is hereby corrected as shown below:

In the Claims

In Claim 4, Column 48, Lines 48-49, delete "close to an end of the column range and opposite from the other volume".

Signed and Sealed this
Twenty-eighth Day of June, 2022

Katherine Kelly Vidal
*Director of the United States Patent and Trademark Office*